(12) United States Patent
Che et al.

(10) Patent No.: US 8,828,984 B2
(45) Date of Patent: Sep. 9, 2014

(54) GOLD(III) COMPLEXES CONTAINING N-HETEROCYCLIC CARBENE LIGAND, SYNTHESIS, AND THEIR APPLICATIONS IN CANCER TREATMENT AND THIOL DETECTION

(71) Applicant: University of Hong Kong, Hong Kong (CN)

(72) Inventors: Chi Ming Che, Hong Kong (CN); Taotao Zou, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 0 days.

(21) Appl. No.: 14/078,742

(22) Filed: Nov. 13, 2013

(65) Prior Publication Data

US 2014/0142080 A1    May 22, 2014

Related U.S. Application Data

(60) Provisional application No. 61/728,039, filed on Nov. 19, 2012.

(51) Int. Cl.
*A61K 31/555* (2006.01)
*C07F 1/12* (2006.01)

(52) U.S. Cl.
USPC ............................................. 514/188; 546/2

(58) Field of Classification Search
USPC ............................................. 514/188; 546/2
See application file for complete search history.

(56) References Cited

U.S. PATENT DOCUMENTS

2013/0193428 A1*  8/2013  Yam et al. ...................... 257/40

OTHER PUBLICATIONS

Sadler, et al. "New trends for metal complexes with anticancer activity." *Curr. Opin. Chem. Biol.* 2008, vol. 12, pp. 197.
Che, et al. "Therapeutic applications of gold complexes: lipophilic gold(III) cations and gold(I) complexes for anti-cancer treatment" *Chem. Commun.* 2011, vol. 47, pp. 9554-9560.
Che, et al. "Gold(III) porphyrins as a new class of anticancer drugs: cytotoxicity, DNA binding and induction of apoptosis in human cervix epitheloid cancer cells" *Chem. Commun.* 2003, pp. 1718-1719.
Berners-Price, Filipovska A. et al, "Mitochondria-targeted chemotherapeutics: the rational design of gold(I) N-heterocyclic carbene complexes that are selectively toxic to cancer cells and target protein selenols in preference to thiols." *J. Am. Chem. Soc.* 2008, vol. 130, pp. 12570-12571.
Fregona, et al. "Gold(III) dithiocarbamate derivatives for the treatment of cancer: solution chemistry, DNA binding, and hemolytic properties." *J. Med. Chem.* 2006, vol. 49, pp. 1648-1657.
Messori, et al. "Thioredoxin reductase: A target for gold compounds acting as potential anticancer drugs" *Coord. Chem. Rev.* 2009, vol. 253, pp. 1692-1707.
Yoon, et al. "Fluorescent and colorimetric probes for detection of thiols" *Chem. Soc. Rev.* 2010, vol. 39, pp. 2120-2135.
Herzenberg, et al. "Glutathione deficiency is associated with impaired survival in HIV disease." *Proc. Natl.Acad. Sci. U. S. A.* 1997, vol. 94, pp. 1967-1972.
Sadler, et al. "The Chemistry of Gold Drugs" *Met Based Drugs* 1994, vol. 1, pp. 107-144.

* cited by examiner

*Primary Examiner* — Charanjit Aulakh
(74) *Attorney, Agent, or Firm* — Leason Ellis LLP

(57) ABSTRACT

Provided herein is a method of synthesis of Au(III)-NHC complexes, a pharmaceutical composition comprises thereof. Also provided herein are the methods for the treatment and prevention of cancer/tumor in patients in need thereof by the administration of the Au(III)-NHC complexes. Also provided is method of detecting thiol in a biological system. The Au(III)-NHC complexes possess anticancer activity such as the induction of cell death, inhibition of cellular proliferation, inhibition of thioredoxin reductase activity, and inhibition of tumor growth in vivo.

35 Claims, 12 Drawing Sheets

9

10

11

12

13

14

15

(A)

(B)

(A)

(B)

(C)

Figure 1:
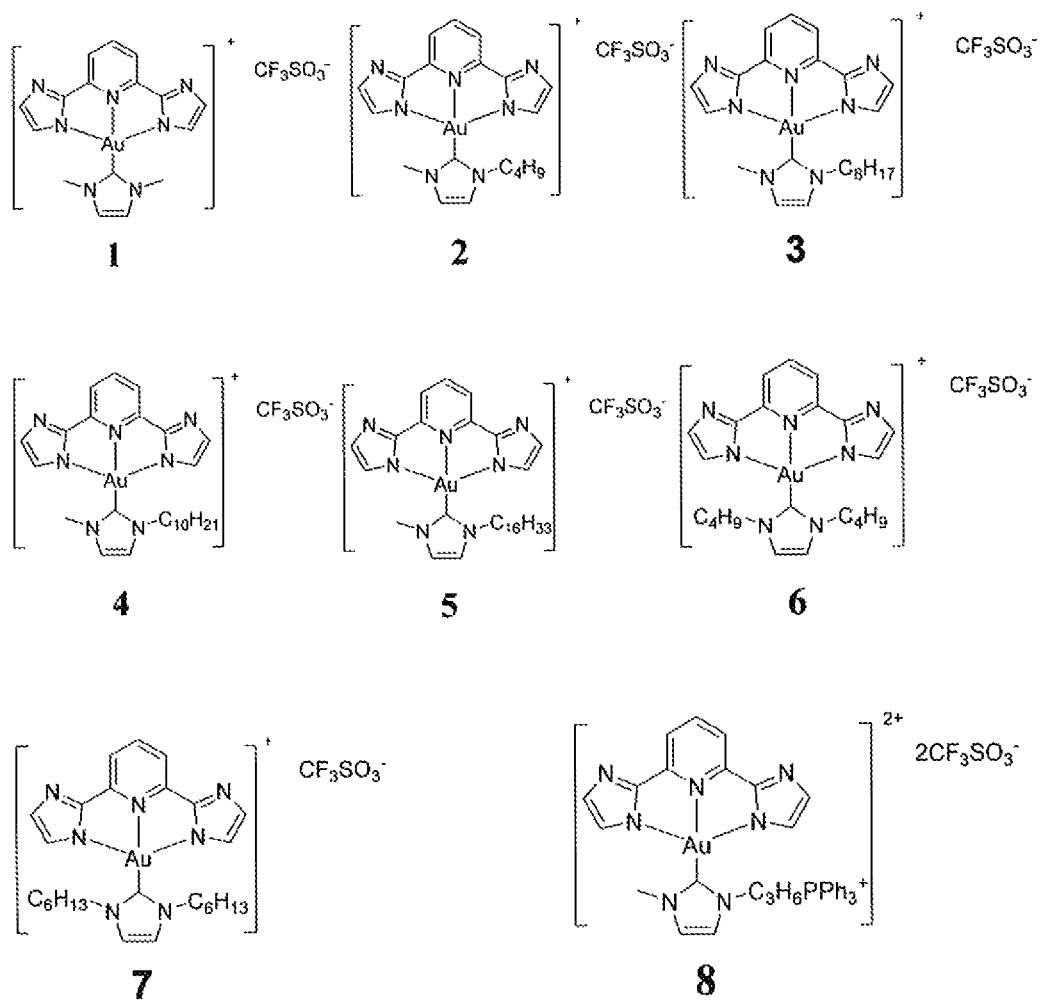
Figure 1B:
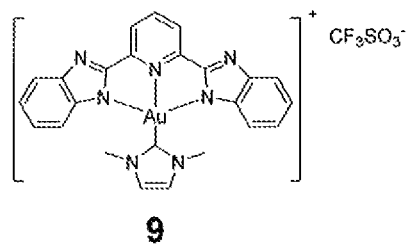
Figure 1B:
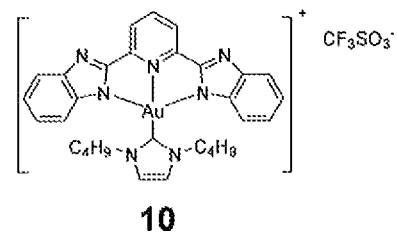
Figure 1B:
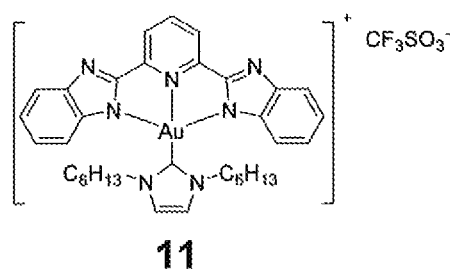
Figure 1B:
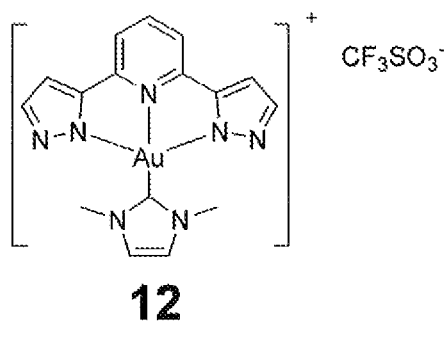
Figure 1B:
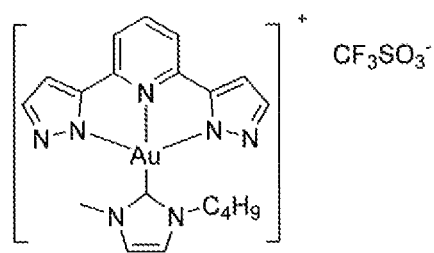
Figure 1B:
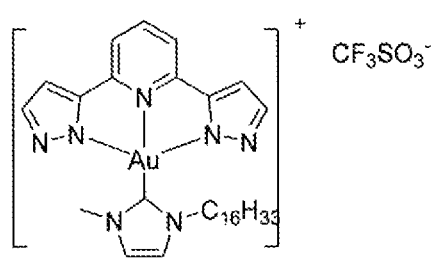
Figure 1B:
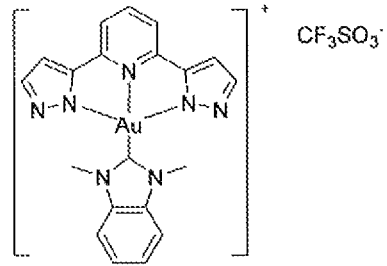

GOLD(III) COMPLEXES CONTAINING N-HETEROCYCLIC CARBENE LIGAND, SYNTHESIS, AND THEIR APPLICATIONS IN CANCER TREATMENT AND THIOL DETECTION

RELATED APPLICATIONS

This application claims the benefit of U.S. provisional application Ser. No. 61/728,039, filed Nov. 19, 2012, which is hereby incorporated by reference in its entirety.

1. INTRODUCTION

Described herein are gold(III) complexes containing N-heterocyclic carbene ligand, a method of synthesis of the gold(III) complexes containing N-heterocyclic carbene ligand, methods of treating and preventing cancer or tumor using the gold(III) complexes containing N-heterocyclic carbene ligand and a method of detecting thiols using the gold (III) complexes containing N-heterocyclic carbene ligand. Also described are therapeutic and prophylactic compositions containing a purified gold(III) complexes containing N-heterocyclic carbene ligand. In certain embodiments, the methods of treating and preventing cancer or tumor are in combination with other cancer or tumor treatment. In certain embodiments, the cancer or tumor treatment is chemotherapy, radiation therapy, gene therapy, surgery or a combination thereof.

2. BACKGROUND

As stimulated by the clinical success of cis-diamminedichloroplatinum (cisplatin), a platinum(II) complex, for the treatment of cancers, scientists have paid great attention to the development of metal-based anticancer drugs which target DNA including the cisplatin analogues and some ruthenium(II)-arene complexes [Sadler, P. J. et al. *Curr. Opin. Chem. Biol.* 2008, 12, 197]. However, severe side effects and the induced drug resistance are commonly encountered and thus subsequently have hampered the wider applications of these DNA binding agents. Recently, some metal complexes including gold(III)-porphyrin [Che, C.-M. et al. *Chem. Commun.* 2011, 47, 9554-9560, Che C.-M. et al. *Chem. Commun.* 2003, 1718-1719.], gold(I)-NHC [J. Berners-Price, S. J., Filipovska A. et al, *J. Am. Chem. Soc.* 2008, 130, 12570-12571] and gold(III) dithiocarbamate [Fregona, D. et al. *J. Med. Chem.* 2006, 49, 1648-1657.] complexes were found to target specific proteins or enzymes, and were capable of overcoming some of the drawbacks of the DNA binding agents by virtue of their different anticancer mechanisms. Despite that numerous previously reported gold(III) complexes like, [Au(bipy)(OH)$_2$]$^+$ (bipy=2,2'-bipyridine), [Messori, L. et al. *Coord. Chem. Rev.* 2009, 253, 1692-1707] showed satisfied antiproliferative ability, examples on in vivo tumor inhibition are sparse.

Fluorescent thiol-sensitive probes have spurred increasing interests especially in biological area, as the cellular thiol level is linked with a great many diseases like cancer, AIDS (Acquired immune deficiency syndrome) and so forth [Yoon, J., *Chem. Soc. Rev.* 2010, 39, 2120-2135; Herzenberg, L. A. et al. *Proc. Natl. Acad. Sci. U.S.A.* 1997, 94, 1967-1972]. Soft metals and metals with tunable redox potentials should be a good starting point to design thiol probes. Gold(III) complexes are always unstable under physiological conditions and will be reduced to Au(I) or even Au(0) by physiological thiols. As Au(III) is usually 4-coordinated but Au(I) is usually 2-coordinated, reduction of Au(III) to Au(I) is accompanied by the release of coordinated ligand(s). If the ligand is highly fluorescent, intraligand emission would be quenched due to the presence of low energy Au(III) 5d$_{x2-y2}$ orbital. Upon reduction of Au(III) to Au(I) by thiols, the fluorescent ligand(s) will be released and switch on the emission.

While the anti-cancer properties of many gold complexes including that of Au(III) and Au(I) are attributed to Au(I), Au(I) ion is unstable under physiological conditions [Sadler, P. J. et al. *Met.-Based Drugs* 1994, 1, 107-144]. The present inventors discovered that N-heterocyclic carbene (NHC) ligand(s) is able to stabilize Au(I) against reduction to Au(0) and/or demetalation under physiological conditions.

As 2,6-bis(1H-benzo[d]imidazol-2-yl)pyridine (H$_2$BPB) and its analogue 2,6-di(1H-imidazol-2-yl)pyridine (H$_2$IPI) and 2,6-di(1H-pyrazol-5-yl)pyridine (H$_2$PPP) are highly emissive and also widely used in biological systems [Che, C.-M. et al. *Chem. Eur. J.* 2010, 16, 6900-6911], the present inventors employ the scaffold to develop novel gold(III) complexes.

Thus, the gold(III) complexes containing multi-dentate N^N^N ligand and NHC moiety provide dual anti-cancer and fluorescent switch-on properties.

3. SUMMARY

Described herein is a method of synthesis of novel Au(III)-NHC complexes, a composition comprising Au(III)-NHC complexes and methods of using the Au(III)-NHC complexes in cancer/tumor treatment and prevention and a method of detecting thiol. In one embodiment, the method of treatment and prevention is in combination with one or more cancer/tumor therapies.

In one embodiment, a method to synthesize cyclometalated N^N^N—Au—Cl, where N^N^N refers to deprotonated 2,6-bis(1H-benzo[d]imidazol-2-yl)pyridine (BPB), 2,6-di(1H-imidazol-2-yl)pyridine (IPI), or 2,6-di(1H-pyrazol-5-yl)pyridine (PPP), and N^N^N—Au—NHC contains two steps:

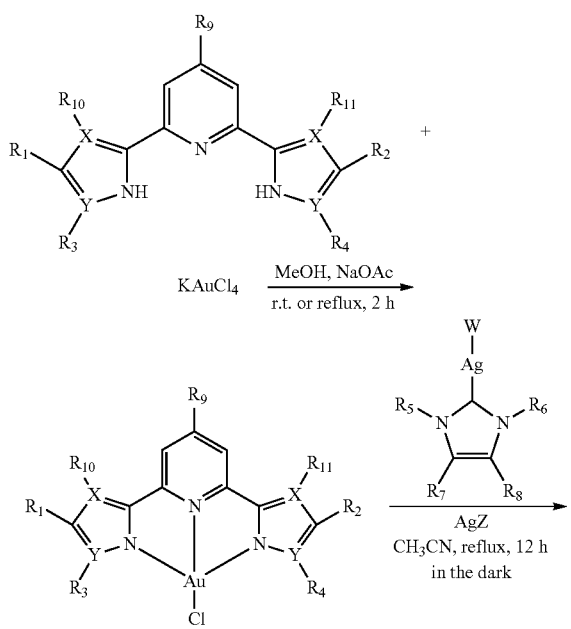

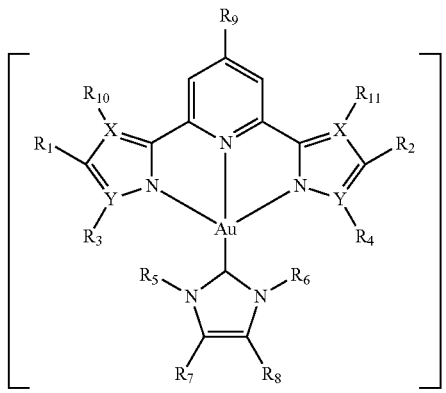

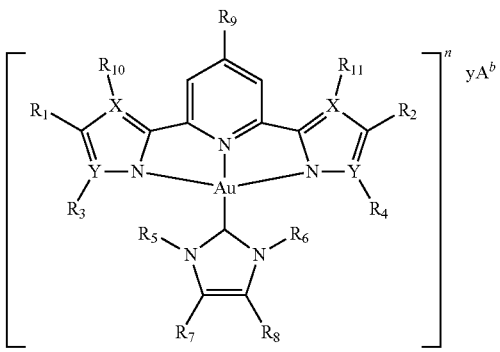

wherein, $R_1$, $R_2$, $R_7$, $R_8$, are each independently selected from the group —H, and $R_3$, $R_4$, $R_{10}$, $R_{11}$ are each dependently selected from an electron pair or —H; or each pair of $R_1$ and $R_3$, $R_2$ and $R_4$, $R_7$ and $R_8$, $R_1$ and $R_{10}$, $R_2$ and $R_{11}$ is independently joined together to form

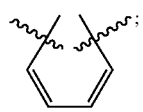

$R_5$, $R_6$, $R_9$, are each independently selected from a —H, —$CH_3$, —$C_4H_9$, —$C_6H_{13}$, —$C_8H_{17}$, —$C_{10}H_{21}$, —$C_{16}H_{33}$, —$C_3H_6PPh_3^+$;

Base refers to an alkali; non-limiting examples of an alkali include NaOAc, NaOH, KOAc, $Na_2CO_3$;

n is an integer ranging from +1 to +2;

y is equal to the absolute value of n/b; and

X is selected from a carbon or a nitrogen atom;

Y is selected from a carbon or a nitrogen atom;

AgZ is a soluble silver(I) salt, non-limiting examples of a silver(I) salt include silver triflate, silver nitrate, silver hexafluorophosphate;

W is selected from Br, I, or Cl.

In another embodiment, provided herein is a method for cancer or tumor treatment and prevention resulting in induction of cell death, inhibition of cellular proliferation, inhibition of thioredoxin reductase or inhibition of in vivo tumor growth. In one embodiment, provided herein is a method comprising administering to a subject in need thereof a composition comprising an effective amount of a Au(III)-NHC complex. In one embodiment, the Au(III)-NHC complexes is a gold(III) complex described herein represented by the structural formulae of I, derivatives thereof; or a pharmaceutically acceptable salt, solvate, or hydrate thereof, wherein, $R_1$, $R_2$, $R_7$, $R_8$, are each independently selected from the group —H, and $R_3$, $R_4$, $R_{10}$, $R_{11}$ are each dependently selected from an electron pair or —H; or each pair of $R_1$ and $R_3$, $R_2$ and $R_4$, $R_7$ and $R_8$, $R_1$ and $R_{10}$, $R_2$ and $R_{11}$ is independently joined together to form

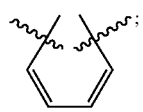

$R_5$, $R_6$, $R_9$, are each independently selected from a —H, —$CH_3$, —$C_4H_9$, —$C_6H_{13}$, —$C_8H_{17}$, —$C_{10}H_{21}$, —$C_{16}H_{33}$, —$C_3H_6PPh_3^+$;

n is an integer ranging from +1 to +2;

y is equal to the absolute value of n/b; and

X is selected from a carbon or a nitrogen atom;

Y is selected from a carbon or a nitrogen atom;

In another embodiment, provided herein is a method for detecting thiol-containing compounds, such as, but not limited to, cysteine (Cys), glutathione (GSH), dithiothreitol (DTT), comprise an effective amount of the Au(III)-NHC complexes, depending on the fluorescence changes at proper wavelength. The Au(III)-NHC complex is a gold(III) complex described herein can be represented by the structural formula of I, or an acceptable salt thereof, wherein,

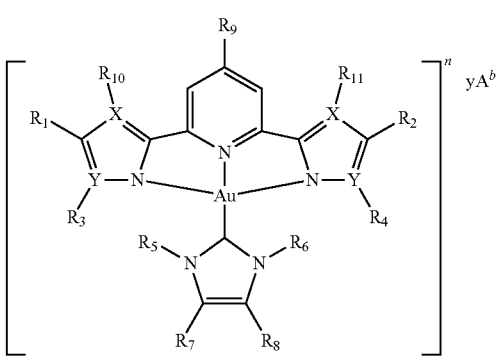

$R_1$, $R_2$, $R_7$, $R_8$, are each independently selected from the group —H, and $R_3$, $R_4$, $R_{10}$, $R_{11}$ are each dependently selected from an electron pair or —H; or each pair of $R_1$ and $R_3$, $R_2$ and $R_4$, $R_7$ and $R_8$, $R_1$ and $R_{10}$, $R_2$ and $R_{11}$ is independently joined together to form

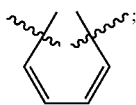

$R_5$, $R_6$, $R_9$, are each independently selected from a —H, —$CH_3$, —$C_4H_9$, —$C_6H_{13}$, —$C_8H_{17}$, —$C_{10}H_{21}$, —$C_{16}H_{33}$, —$C_3H_6PPh_3^+$;

n is an integer ranging from +1 to +2;

y is equal to the absolute value of n/b; and

X is selected from a carbon or a nitrogen atom;

Y is selected from a carbon or a nitrogen atom.

The Au(III)-NHC complexes are stable in air and aqueous solutions like phosphate-buffered saline (PBS) conditions. They are very sensitive to physiological thiols and can be reduced to generate the anti-cancer active Au(I)-NHC complexes which are relatively inert to excel thiols, and the reduction process is also accompanied with the release of highly fluorescent ligand. The Au(III)-NHC complexes display similar anti-cancer or anti-tumor activity to the clinically used cisplatin and can inhibit the tumor growth of mice bearing HeLa xenograft. The release of the fluorescent ligand upon Au(III) to Au(I) reduction in the presence of thiols leads them to be excellent bio-probes to detect physiological thiols. In addition, the ease of syntheses (2 steps) and structural modification also helps these complexes for prevalent biological applications.

4. BRIEF DESCRIPTION OF THE DRAWINGS

FIGS. 1 (A) and (B) show Chemical structures of the Au(III)-NHC complexes.

Figure 2:
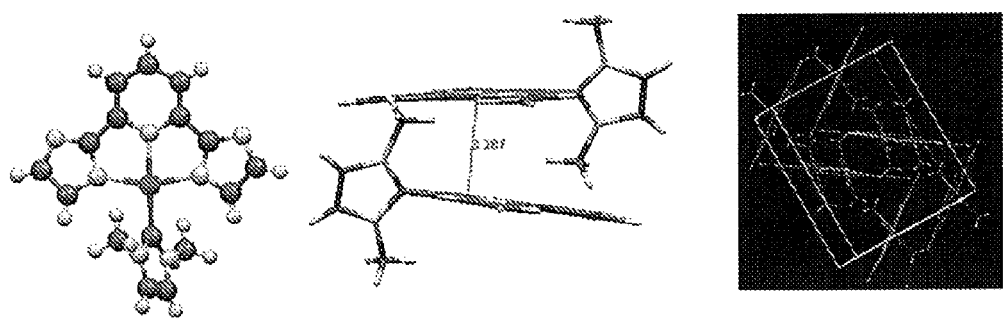
Figure 2:
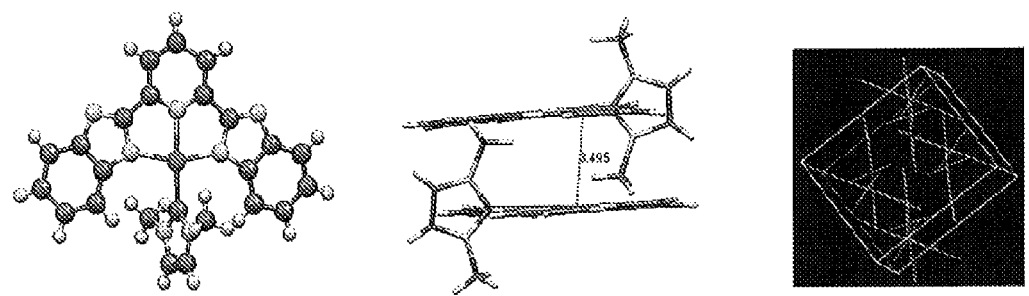

FIGS. 2(A) and (B) show Crystal structure of 1 (A) and 9 (B)

Figure 3A:
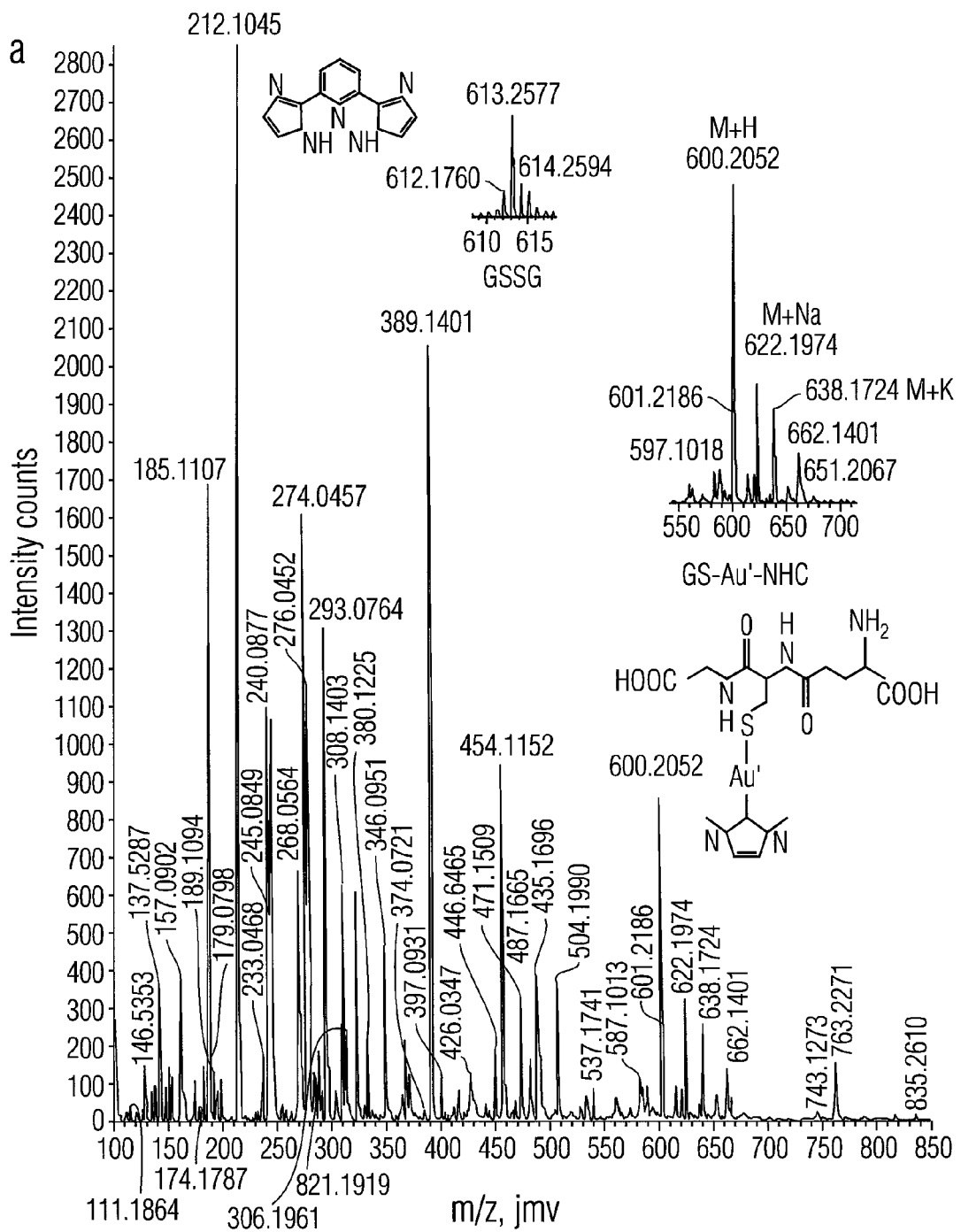
Figure 3B:
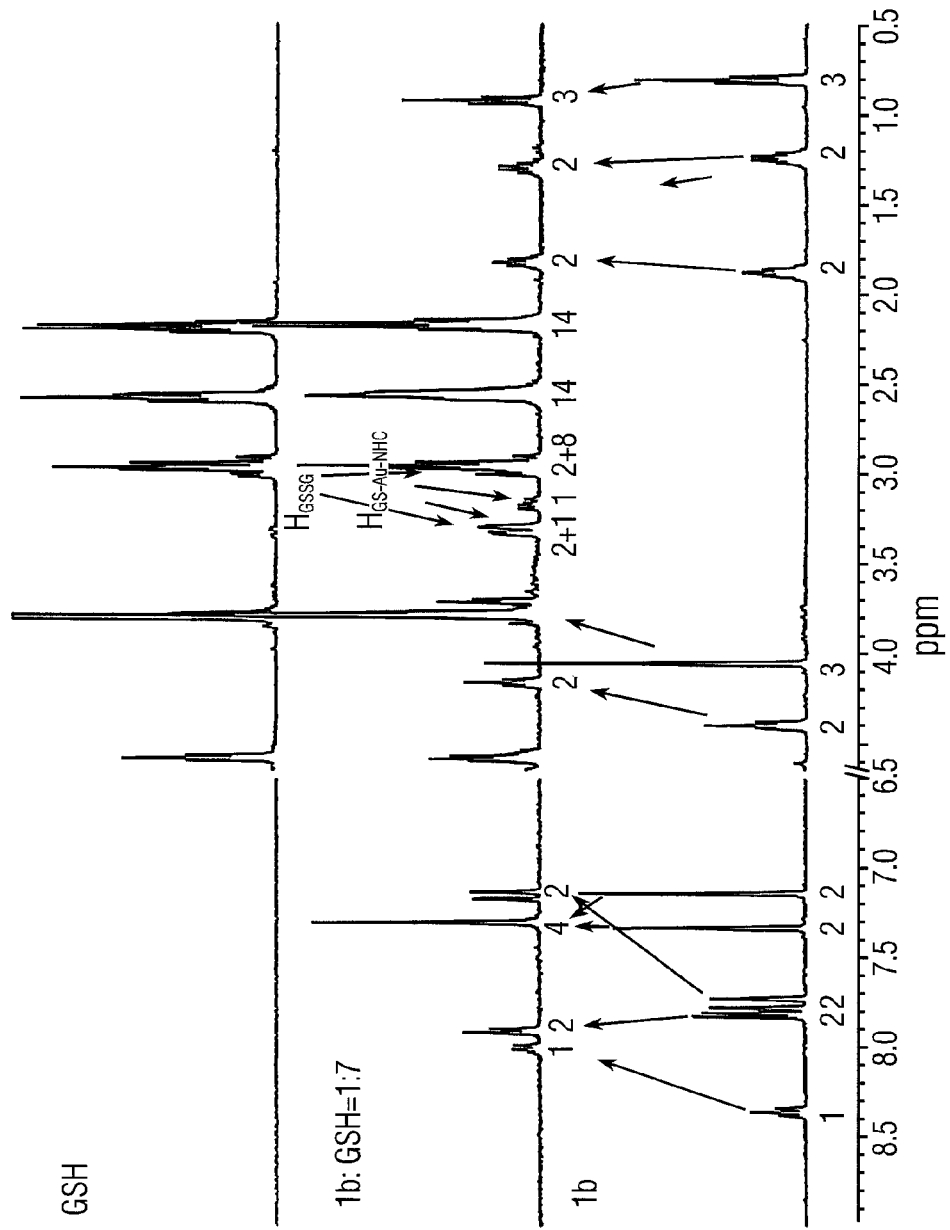
Figure 3C:
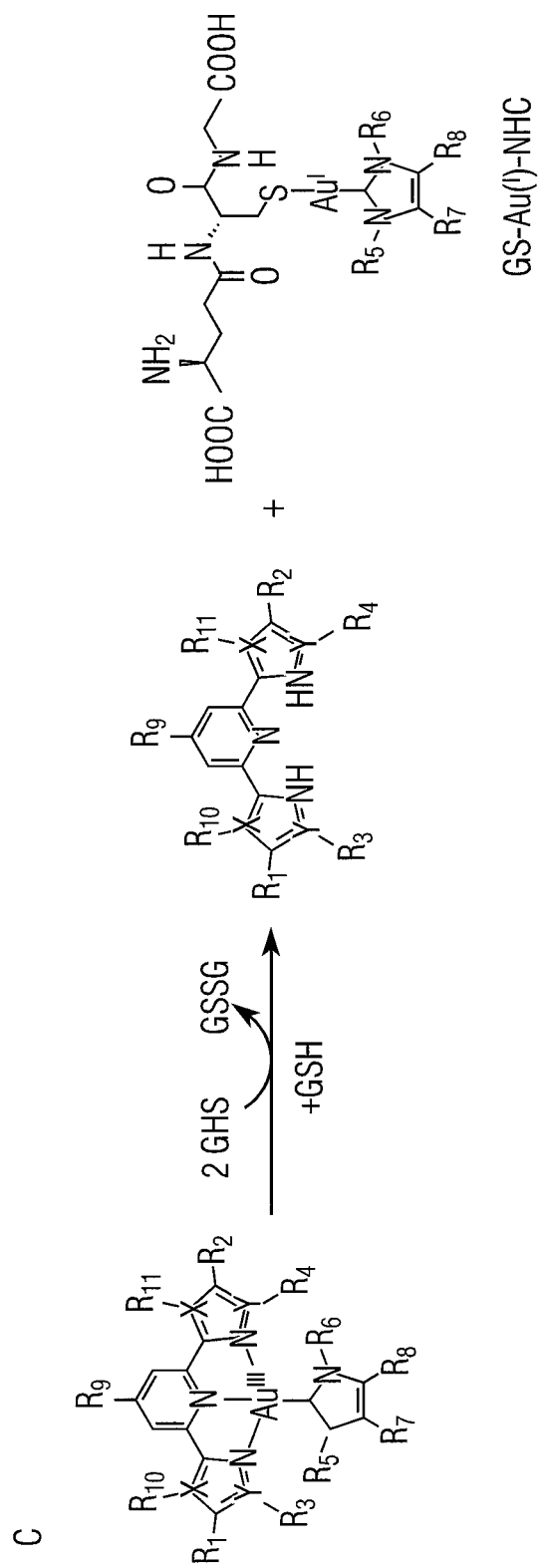

FIGS. 3(A)-(C) show A) ESI-MS analysis of the mixture of 1 and GSH. B) $^1$H NMR spectra (400 MHz) of free GSH (top), a mixture of GSH and 2 in a 7:1 molar ratio after mixing for 10 min (middle), and 2 (bottom); intensity ratios are shown. (C) Proposed reaction of the Au(III)-NHC complexes with GSH under physiological like conditions.

Figure 4A:
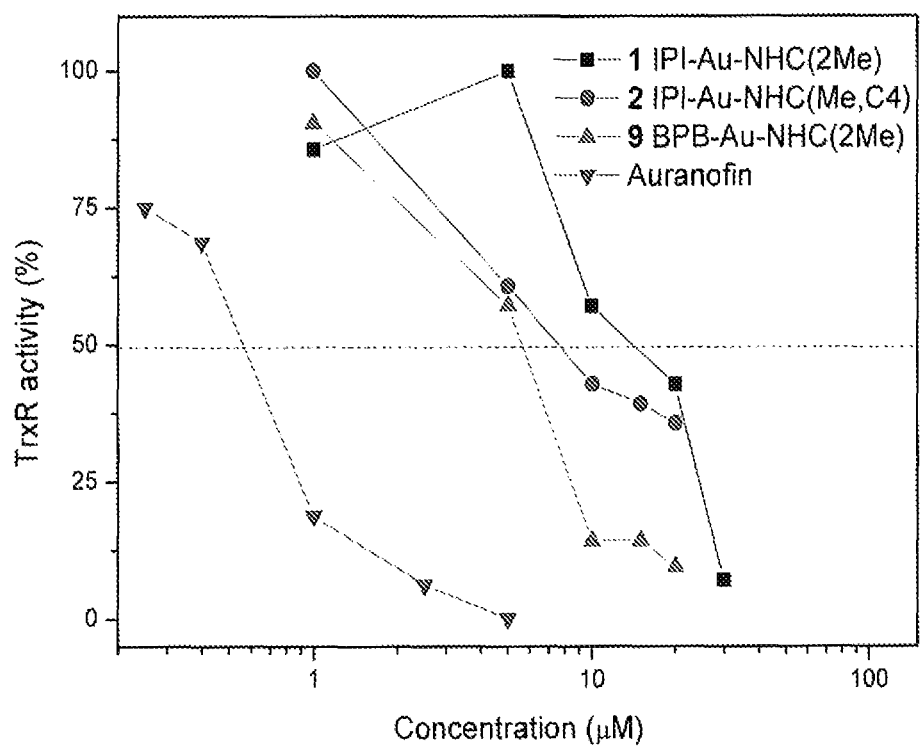
Figure 4B:
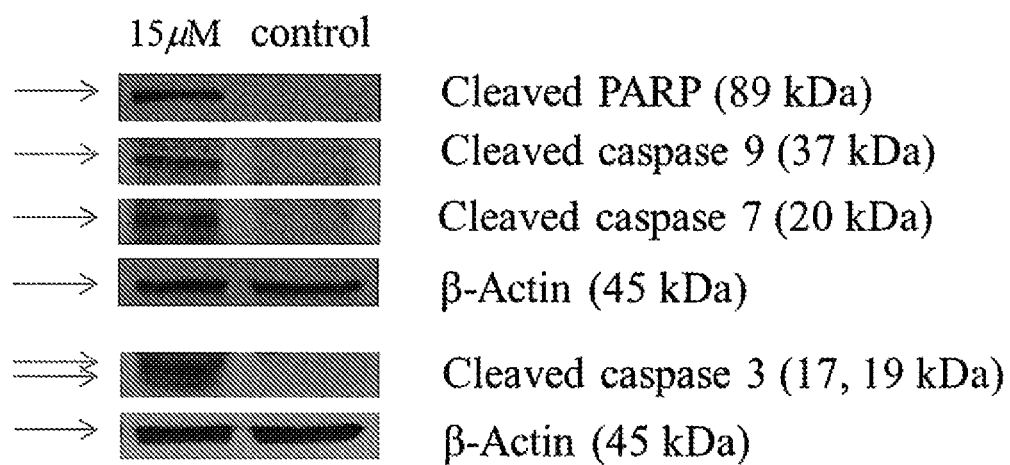
Figure 4C:
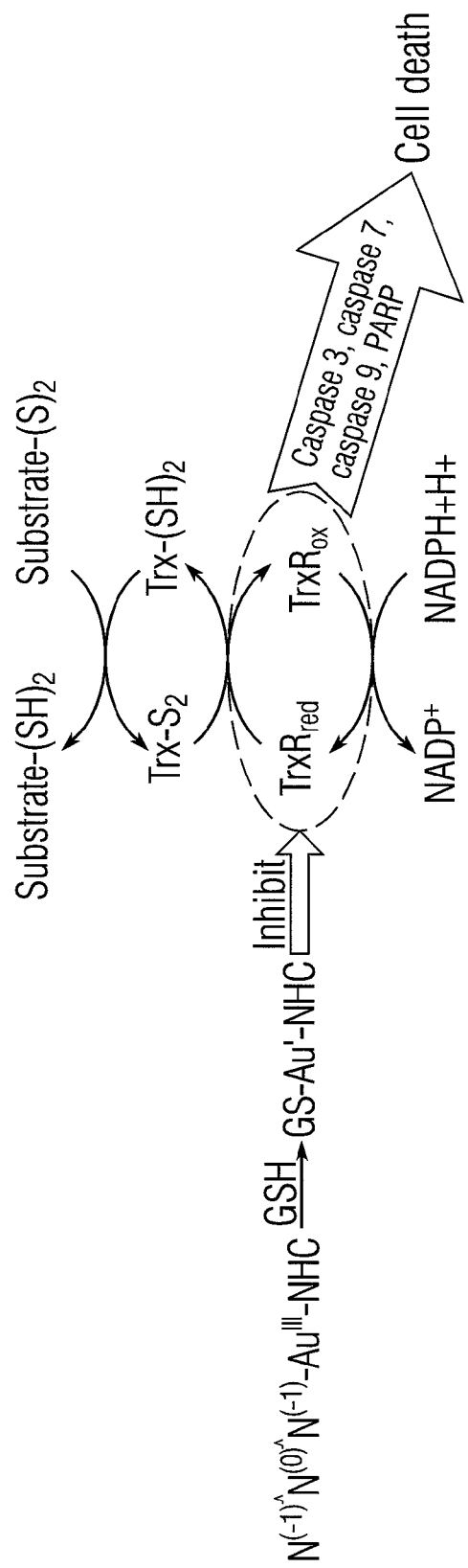

FIGS. 4(A)-(C) show A) Cell based TrxR activity for 1 (IPI-Au-NHC(2Me)), 2 (IPI-Au-NHC(Me, C4)) and 9 (BPB-Au-NHC(2Me)) after treating for 1 h. B) Western blotting results of 9 towards PARP, caspase 9, caspase 7, caspase 3. C) Proposed anticancer pathway FIGS. 5(A)-(D) show In vivo tumor inhibition effect: A). Graphic representation of tumor volume changes after treating mice bearing HeLa xenograft with 3 mg/kg of 5 or solvent; B) Body weight changes after treating mice bearing HeLa xenograft with 3 mg/kg of 5 or solvent; C) & D) Photos of mouse tumors in different groups.

FIGS. 6(A)-(C) show A) Fluorescence intensity before (red) and after (blue) adding GSH or Cys (2 mM) into 20 μM of 9 in PBS:DMSO=9:1 (v/v). B) Fluorescence response of 9 towards different analysts. C) Fluorescence microscopy images of HeLa cells after treating with 20 μM of 9 for 10 min.

5. DETAILED DESCRIPTION

Disclosed are the synthesis of novel gold(III) [or Au(III) or Au$^{3+}$] complexes containing N-heterocyclic carbene ligand (NHC), novel gold(III) [or Au(III) or Au$^{3+}$] complexes containing N-heterocyclic carbene ligand (NHC), composition comprising novel gold(III) [or Au(III) or Au$^{3+}$] complexes containing N-heterocyclic carbene ligand (NHC), methods of treating and preventing cancer or tumor in a subject, and a method of detecting thiol. Disclosed herein is a method of treating or preventing cancer/tumor comprising administering a pharmaceutical composition comprising at least one of the Au(III)-NHC complexes in an effective amount for anti-cancer or anti-tumor activity. In certain embodiments, anti-cancer or anti-tumor activities includes, but are not limited to, the induction of cell death, inhibition of cellular proliferation, inhibition of thioredoxin reductase and/or poisoning of thioredoxin reductase, and inhibition of in vivo tumor growth. Provided herein is a method of detecting thiol which comprises detecting thiol containing compounds using at least one of the Au(III)-NHC complexes. In an embodiment, a signal is detected depending on fluorescence changes at proper wavelength. As provided herein, in one embodiment, Au(III)-NHC complexes refer to a molecule of a gold(III) ion connected to a tridentate ligand and N-heterocyclic carbene ligand. In one embodiment, gold(III) [or Au(III) or Au$^{3+}$] complexes containing N-heterocyclic carbene ligand (NHC) is represented by structural formula I, derivatives thereof; or a pharmaceutically acceptable salt, solvate, or hydrate thereof.

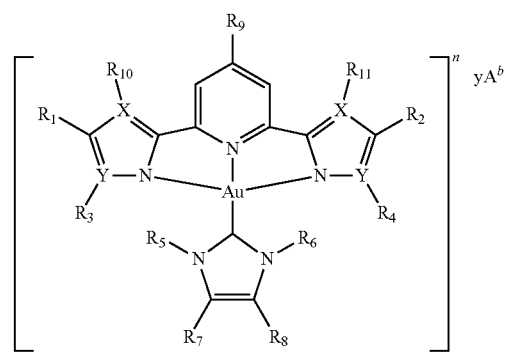

I $R_1$, $R_2$, $R_7$, $R_8$, are each independently selected from the group —H, and $R_3$, $R_4$, $R_{10}$, $R_{11}$ are each dependently selected from an electron pair or —H; or each pair of $R_1$ and $R_3$, $R_2$ and $R_4$, $R_7$ and $R_8$, $R_1$ and $R_{10}$, $R_2$ and $R_{11}$ is independently joined together to form

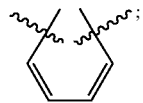

$R_5$, $R_6$, $R_9$, are each independently selected from a —H, —$CH_3$, —$C_4H_9$, —$C_6H_{13}$, —$C_8H_{17}$, —$C_{10}H_{21}$, —$C_{16}H_{33}$, —$C_3H_6PPh_3^+$;

n is an integer ranging from +1 to +2;

y is equal to the absolute value of n/b; and

X is selected from a carbon or a nitrogen atom;

Y is selected from a carbon or a nitrogen atom;

As used herein, the term "tridentate ligand" refers to a di-anionic substituted/non-substituted 2,6-bis(1H-benzo[d] imidazol-2-yl)pyridine ($H_2$BPB) and its analogue 2,6-di(1H-imidazol-2-yl)pyridine ($H_2$IPI), 2,6-di(1H-pyrazol-5-yl)pyridine ($H_2$PPP) ligand. Non-limiting examples of the deprotonated N^N^N ligands are:

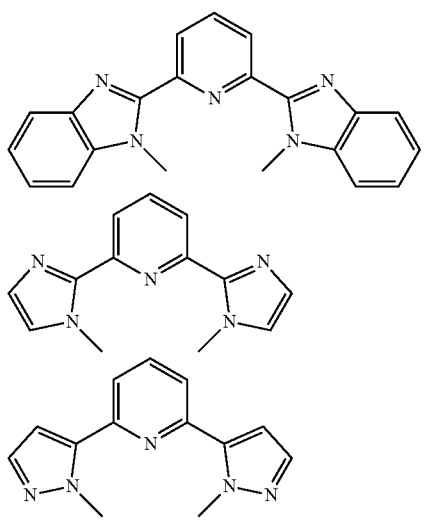

As used herein, the term "N-heterocyclic carbene" refers to a ligand having one of the following chemical structures:

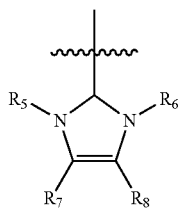

Wherein $R_5$, $R_6$ are each independently selected from a —$CH_3$, —$C_4H_9$, —$C_6H_{13}$, —$C_8H_{17}$, —$C_{10}H_{21}$, —$C_{16}H_{33}$, —$C_3H_6PPh_3^+$ $R_7$, $R_8$ are each independently selected from the group consisting of —H; or the pair $R_7$, $R_8$ is joined together to form

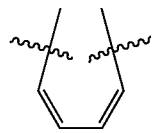 [SMILES: */C=C\C=C/*]

It will be understood that the di-anionic N^N^N ligand can form a non-neutral complex with the gold(III) ion. For instance, the net positive charge on the gold(III) can be greater than the absolute net negative charge of the N^N^N ligand. In view of this, there can be at least one counter-anion coordinated to the Au(III)-NHC complex for charge neutralization.

Accordingly, the phrase "acceptable salt," as used herein, includes salts formed from the charged Au(III)-NHC complex and counter-anion(s).

As used herein, the phrase "counter-anion" refers to an ion associated with a positively charged Au(III)-NHC complex. Non-limiting examples of counter-ions include halogens such as fluoride (F⁻), chloride (Cl⁻), bromide (Br⁻), iodide (I⁻); sulfate ($SO_4^{2-}$); phosphate ($PO_4^{3-}$); trifluoromethanesulfonate (triflate, ⁻OTf or $CF_3SO_3^-$); acetate (⁻OAc); nitrate ($NO_3^-$); perchlorate ($ClO_4^-$); hexafluorophosphate ($PF_6^-$) and hexafluoroacetylacetonate ($[CF_3C(O)CHC(O)CF_3]^-$).

In one embodiment, the invention relates to the synthesis of novel gold(III) [or Au(III) or $Au^{3+}$] bearing N-heterocyclic carbene ligand.

In another embodiment, the invention relates to a pharmaceutical composition for cancer treatment by inhibition of the proliferation of cancer cells in vitro comprising an effective amount of one or more of the Au(III)-NHC complexes.

In another embodiment, the invention relates to a pharmaceutical for cancer treatment by inhibition or poisoning of thioredoxin reductase comprising an effective amount of one or more of the Au(III)-NHC complexes.

In another embodiment, the invention relates to a pharmaceutical composition for cancer treatment by the inhibition of tumor growth in vivo comprising an effective amount of one or more of the Au(III)-NHC complexes.

In another embodiment, the invention relates to fluorescent detecting thiol-containing compounds such as cysteine (Cys), glutathione (GSH), dithiothreitol (DTT), and the application in cellular thiol imaging, comprising an effective amount of a Au(III)-NHC complex.

The Au(III)-NHC complexes of this invention can be represented by one or more of structural formula I, derivatives thereof; or a pharmaceutically acceptable salt, solvate, or hydrate thereof.

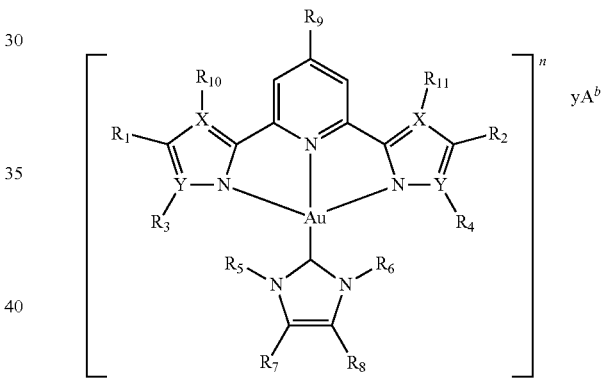

$R_1$, $R_2$, $R_7$, $R_8$, are each independently selected from the group —H, and $R_3$, $R_4$, $R_{10}$, $R_{11}$ are each dependently selected from an electron pair or —H; or each pair of $R_1$ and $R_3$, $R_2$ and $R_4$, $R_7$ and $R_8$, $R_1$ and $R_{10}$, $R_2$ and $R_{11}$ is independently joined together to form

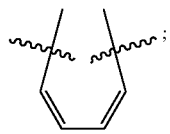 [SMILES: */C=C\C=C/*]

$R_5$, $R_6$, $R_9$, are each independently selected from a —H, —$CH_3$, —$C_4H_9$, —$C_6H_{13}$, —$C_8H_{17}$, —$C_{10}H_{21}$, —$C_{16}H_{33}$, —$C_3H_6PPh_3^+$;

n is an integer ranging from +1 to +2;

y is equal to the absolute value of n/b; and

X is selected from a carbon or a nitrogen atom;

Y is selected from a carbon or a nitrogen atom.

In one embodiment, the invention relates to a pharmaceutical composition for treating or preventing cancer/tumor. In certain embodiments, the treatment and prevention comprises induction of cell death, inhibition of cellular proliferation, inhibition of thioredoxin reductase and/or poisoning of thioredoxin reductase, and the inhibition of tumor growth in vivo. In one embodiment, the method comprises administering an effective amount of the Au(III)-NHC complexes to a subject. In one embodiment, the method comprises detecting physiological thiol-containing compounds, including but are not limited to, cysteine (Cys), glutathione (GSH), dithiothreitol (DTT), with an effective amount of the Au(III)-NHC complexes, In one embodiment, thiol is detected by fluorescence changes at proper wavelength. The Au(III)-NHC complex has a formula I, derivatives thereof; or a pharmaceutically acceptable salt, solvate, or hydrate thereof, wherein, X is a nitrogen atom;
Y is a carbon atom;
$R_{10}$, $R_{11}$ are each lone electron pairs;
$R_1$, $R_2$, $R_3$, $R_4$, $R_7$, $R_8$, $R_9$ are each —H;
$R_5$, $R_6$ are each —$CH_3$;
n is +1, and
$yA^b$ is $CF_3SO_3^-$. (Complex 1)

In another embodiment, described herein is a pharmaceutical composition for treatment or prevention of cancer/tumor. In certain embodiment, the treatment or prevention comprises induction of cell death, inhibition of cellular proliferation, inhibition of thioredoxin reductase and/or poisoning of thioredoxin reductase, and the inhibition of tumor growth in vivo. The method comprises administering to a subject an effective amount of the Au(III)-NHC complexes. In one embodiment, the method detects physiological thiol-containing compounds which includes, but not limited to, cysteine (Cys), glutathione (GSH), dithiothreitol (DTT), with an effective amount of the Au(III)-NHC complexes. In one embodiment, the detection comprises fluorescence changes at proper wavelength. The Au(III)-NHC complex has a formula I, derivatives thereof; or a pharmaceutically acceptable salt, solvate, or hydrate thereof, wherein, X is a nitrogen atom;
Y is a carbon atom;
$R_{10}$, $R_{11}$ are each lone electron pairs;
$R_1$, $R_2$, $R_3$, $R_4$, $R_7$, $R_8$, $R_9$ are each —H;
$R_5$ is —$CH_3$;
$R_6$ is —$C_4H_9$;
n is +1, and
$yA^b$ is $CF_3SO_3^-$. (Complex 2)

In another embodiment, provided herein is a pharmaceutical composition for treatment or prevention of cancer/tumor. The method includes for example, induction of cell death, inhibition of cellular proliferation, inhibition of thioredoxin reductase and/or poisoning of thioredoxin reductase, and the inhibition of tumor growth in vivo. The method comprises administering an effective amount of the Au(III)-NHC complexes to a subject. In one embodiment, the method comprises detecting physiological thiol-containing compounds including, but not limited to, cysteine (Cys), glutathione (GSH), dithiothreitol (DTT), with an effective amount of the Au(III)-NHC complexes. In one embodiment, the detection comprises fluorescence changes at proper wavelength. The Au(III)-NHC complex has a formula I, derivatives thereof; or a pharmaceutically acceptable salt, solvate, or hydrate thereof, wherein, X is a nitrogen atom;
Y is a carbon atom;
$R_{10}$, $R_{11}$ are each lone electron pairs;
$R_1$, $R_2$, $R_3$, $R_4$, $R_7$, $R_8$, $R_9$ are each —H;
$R_5$ is —$CH_3$;
$R_6$ is —$C_8H_{17}$;
n is +1, and
$yA^b$ is $CF_3SO_3^-$. (Complex 3)

In another embodiment, provided herein is a pharmaceutical composition for treatment and prevention of cancer/tumor. In certain embodiment, the treatment and prevention comprises induction of cell death, inhibition of cellular proliferation, inhibition of thioredoxin reductase and/or poisoning of thioredoxin reductase, and the inhibition of tumor growth in vivo. In an embodiment, the method comprises administering to a subject an effective amount of the Au(III)-NHC complexes. In one embodiment, the method comprises detecting physiological thiol-containing compounds including, but not limited to, cysteine (Cys), glutathione (GSH), dithiothreitol (DTT), with an effective amount of the Au(III)-NHC complexes. In one embodiment, the detection comprises fluorescence changes at proper wavelength. The Au(III)-NHC complex has a formula I, derivatives thereof; or a pharmaceutically acceptable salt, solvate, or hydrate thereof, wherein, X is a nitrogen atom;
Y is a carbon atom;
$R_{10}$, $R_{11}$ are each lone electron pairs;
$R_1$, $R_2$, $R_3$, $R_4$, $R_7$, $R_8$, $R_9$ are each —H;
$R_5$ is —$CH_3$;
$R_6$ is —$C_{10}H_{21}$;
n is +1, and
$yA^b$ is $CF_3SO_3^-$. (Complex 4)

In another embodiment, provided herein is a pharmaceutical composition for treatment and prevention of cancer/tumor. In certain embodiment, the treatment and prevention comprises induction of cell death, inhibition of cellular proliferation, inhibition of thioredoxin reductase and/or poisoning of thioredoxin reductase, and the inhibition of tumor growth in vivo. The method comprises administering to a subject an effective amount of the Au(III)-NHC complexes. In an embodiment, the method comprises detecting physiological thiol-containing compounds including, but are not limited to, cysteine (Cys), glutathione (GSH), dithiothreitol (DTT), with an effective amount of the Au(III)-NHC complexes. In one embodiment, the method comprises fluorescence changes at proper wavelength. In one embodiment, the Au(III)-NHC complex has a formula I, derivatives thereof; or a pharmaceutically acceptable salt, solvate, or hydrate thereof, wherein, X is a nitrogen atom;
Y is a carbon atom;
$R_{10}$, $R_{11}$ are each lone electron pairs;
$R_1$, $R_2$, $R_3$, $R_4$, $R_7$, $R_8$, $R_9$ are each —H;
$R_5$ is —$CH_3$;
$R_6$ is —$C_{16}H_{33}$;
n is +1, and
$yA^b$ is $CF_3SO_3^-$. (Complex 5)

In another embodiment, provided herein is a pharmaceutical composition for treatment and prevention of cancer/tumor. In certain embodiments, the method comprises induction of cell death, inhibition of cellular proliferation, inhibition of thioredoxin reductase and/or poisoning of thioredoxin reductase, and the inhibition of tumor growth in vivo. In one embodiment, the method comprises administering to a subject an effective amount of the Au(III)-NHC complexes. In one embodiment; the method comprises detecting physiological thiol-containing compounds including, but are not limited to, cysteine (Cys), glutathione (GSH), dithiothreitol (DTT), with an effective amount of the Au(III)-NHC complexes. In one embodiment, the method comprises fluorescence changes at proper wavelength. In one embodiment, the Au(III)-NHC complex has a formula I, derivatives thereof; or a pharmaceutically acceptable salt, solvate, or hydrate thereof, wherein, X is a nitrogen atom;
Y is a carbon atom;
$R_{10}$, $R_{11}$ are each lone electron pairs;
$R_1$, $R_2$, $R_3$, $R_4$, $R_7$, $R_8$, $R_9$ are each —H;
$R_5$, $R_6$ are each —$C_4H_9$;
n is +1, and
$yA^b$ is $CF_3SO_3^-$. (Complex 6)

In another embodiment, provided herein is a pharmaceutical composition for treatment and prevention of cancer/tumor. In certain embodiments, the method comprises induction of cell death, inhibition of cellular proliferation, inhibition of thioredoxin reductase and/or poisoning of thioredoxin reductase, and the inhibition of tumor growth in vivo. In one embodiment, the method comprises administering to a subject an effective amount of the Au(III)-NHC complexes. In one embodiment, the method comprises detecting physiological thiol-containing compounds including, but are not limited to, cysteine (Cys), glutathione (GSH), dithiothreitol (DTT), with an effective amount of the Au(III)-NHC complexes. In one embodiment, the method comprises detecting fluorescence changes at proper wavelength. The Au(III)-NHC complex has a formula I, derivatives thereof; or a pharmaceutically acceptable salt, solvate, or hydrate thereof, wherein,
X is a nitrogen atom;
Y is a carbon atom;
$R_{10}$, $R_{11}$ are each lone electron pairs;
$R_1$, $R_2$, $R_3$, $R_4$, $R_7$, $R_8$, $R_9$ are each —H;
$R_5$, $R_6$ are each —$C_6H_{13}$;
n is +1, and
$yA^b$ is $CF_3SO_3^-$. (Complex 7)

In another embodiment, provided herein is a pharmaceutical composition for treatment or prevention of cancer/tumor. In certain embodiments, the method comprises induction of cell death, inhibition of cellular proliferation, inhibition of thioredoxin reductase and/or poisoning of thioredoxin reductase, and the inhibition of tumor growth in vivo. In one embodiment, the method comprises administering to a subject an effective amount of the Au(III)-NHC complexes. In one embodiment, the method comprises detecting physiological thiol-containing compounds including, but not limited to, cysteine (Cys), glutathione (GSH), dithiothreitol (DTT), with an effective amount of the Au(III)-NHC complexes. In one embodiment, the method comprises detecting fluorescence changes at proper wavelength. The Au(III)-NHC complex has a formula I, derivatives thereof; or a pharmaceutically acceptable salt, solvate, or hydrate thereof, wherein,
X is a nitrogen atom;
Y is a carbon atom;
$R_{10}$, $R_{11}$ are each lone electron pairs;
$R_1$, $R_2$, $R_3$, $R_4$, $R_7$, $R_8$, $R_9$ are each —H;
$R_5$ is —$CH_3$;
$R_6$ is —$C_3H_6PPh_3^+$;
n is +2, and
$yA^b$ is $2CF_3SO_3^-$. (Complex 8)

In another embodiment, described herein is a pharmaceutical composition for treatment and prevention of cancer/tumor. In certain embodiments, the method comprises induction of cell death, inhibition of cellular proliferation, inhibition of thioredoxin reductase and/or poisoning of thioredoxin reductase, and the inhibition of tumor growth in vivo. In an embodiment, the method comprises administering to a subject an effective amount of the Au(III)-NHC complexes. In one embodiment, the method comprises detecting physiological thiol-containing compounds including, but are not limited to, cysteine (Cys), glutathione (GSH), dithiothreitol (DTT), with an effective amount of the Au(III)-NHC complexes. In one embodiment, the method comprises detecting fluorescence changes at proper wavelength. The Au(III)-NHC complex has a formula I, derivatives thereof; or a pharmaceutically acceptable salt, solvate, or hydrate thereof, wherein,
X is a nitrogen atom;
Y is a carbon atom;
Each pair of $R_1$ and $R_3$, and $R_2$ and $R_4$ is joined together to form

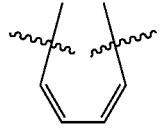 [SMILES: */C=C\C=C/*]

$R_7$, $R_8$, $R_9$ are each —H;
$R_{10}$, $R_{11}$ are each lone electron pairs;
$R_5$, $R_6$ are each —$CH_3$;
n is +1, and
$yA^b$ is $CF_3SO_3^-$. (Complex 9)

In another embodiment, provided herein is a pharmaceutical composition for treatment and prevention of cancer/tumor. In certain embodiments, the method comprises induction of cell death, inhibition of cellular proliferation, inhibition of thioredoxin reductase and/or poisoning of thioredoxin reductase, and the inhibition of tumor growth in vivo. In one embodiment, the method comprises administering to a subject an effective amount of the Au(III)-NHC complexes. In one embodiment, the method comprises detecting physiological thiol-containing compounds including, but not limited to, cysteine (Cys), glutathione (GSH), dithiothreitol (DTT), with an effective amount of the Au(III)-NHC complexes. In one embodiment, the method comprises detecting fluorescence changes at proper wavelength. The Au(III)-NHC complex has a formula I, derivatives thereof; or a pharmaceutically acceptable salt, solvate, or hydrate thereof, wherein,
X is a nitrogen atom;
Y is a carbon atom;
Each pair of $R_1$ and $R_3$, and $R_2$ and $R_4$ is joined together to form

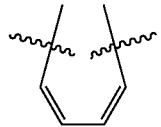 [SMILES: */C=C\C=C/*]

$R_7$, $R_8$, $R_9$ are each —H;
$R_{10}$, $R_{11}$ are each lone electron pairs;
$R_5$, $R_6$ are each —$C_4H_9$;
n is +1, and
$yA^b$ is $CF_3SO_3^-$. (Complex 10)

In another embodiment, provided herein is a pharmaceutical composition for treatment and prevention of cancer/tumor. In certain embodiments, the method comprises induction of cell death, inhibition of cellular proliferation, inhibition of thioredoxin reductase and/or poisoning of thioredoxin reductase, and the inhibition of tumor growth in vivo. In one embodiment, the method comprises administering to a subject an effective amount of the Au(III)-NHC complexes. In one embodiment, the method comprises detecting physiological thiol-containing compounds including, but not limited to, cysteine (Cys), glutathione (GSH), dithiothreitol (DTT), with an effective amount of the Au(III)-NHC complexes. In one embodiment, the method comprises detecting fluorescence changes at proper wavelength. The Au(III)-NHC complex has a formula I, derivatives thereof; or a pharmaceutically acceptable salt, solvate, or hydrate thereof, wherein, X is a nitrogen atom;
Y is a carbon atom;
Each pair of $R_1$ and $R_3$, and $R_2$ and $R_4$ is joined together to form

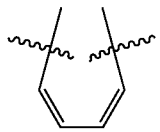 [SMILES: */C=C\C=C/*]

$R_7$, $R_8$, $R_9$ are each —H;
$R_{10}$, $R_{11}$ are each lone electron pairs;
$R_5$, $R_6$ are each —$C_6H_{13}$;
n is +1, and
$yA^b$ is $CF_3SO_3^-$. (Complex 11)

In another embodiment, provided herein is a pharmaceutical composition for treatment and prevention of cancer/tumor. In certain embodiments, the method comprises induction of cell death, inhibition of cellular proliferation, inhibition of thioredoxin reductase and/or poisoning of thioredoxin reductase, and the inhibition of tumor growth in vivo. In one embodiment, the method comprises administering to a subject an effective amount of the Au(III)-NHC complexes. In one embodiment, the method comprises detecting physiological thiol-containing compounds including, but not limited to, cysteine (Cys), glutathione (GSH), dithiothreitol (DTT), with an effective amount of the Au(III)-NHC complexes. In one embodiment, the method comprises detecting fluorescence changes at proper wavelength. The Au(III)-NHC complex has a formula I, derivatives thereof; or a pharmaceutically acceptable salt, solvate, or hydrate thereof, wherein, X is a carbon atom;
Y is a nitrogen atom;
$R_3$, $R_4$ are each lone electron pairs;
$R_1$, $R_2$, $R_7$, $R_8$, $R_9$, $R_{10}$, $R_{11}$ are each —H;
$R_5$, $R_6$ are each —$CH_3$;
n is +1, and
$yA^b$ is $CF_3SO_3^-$. (Complex 12)

In another embodiment, provided herein is a pharmaceutical composition for treatment and prevention of cancer/tumor. In certain embodiment, the method comprises induction of cell death, inhibition of cellular proliferation, inhibition of thioredoxin reductase and/or poisoning of thioredoxin reductase, and the inhibition of tumor growth in vivo. In an embodiment, the method comprises administration to a subject an effective amount of the Au(III)-NHC complexes. In one embodiment, the method comprises detecting physiological thiol-containing compounds including, but not limited to, cysteine (Cys), glutathione (GSH), dithiothreitol (DTT), with an effective amount of the Au(III)-NHC complexes. In one embodiment, the method comprises detecting fluorescence changes at proper wavelength. The Au(III)-NHC complex has a formula I, derivatives thereof; or a pharmaceutically acceptable salt, solvate, or hydrate thereof, wherein, X is a carbon atom;
Y is a nitrogen atom;
$R_3$, $R_4$ are each lone electron pairs;
$R_1$, $R_2$, $R_7$, $R_8$, $R_9$, $R_{10}$, $R_{11}$ are each —H;
$R_5$ is —$CH_3$;
$R_6$ is —$C_4^{14}H_9$;
n is +1, and
$yA^b$ is $CF_3SO_3^-$. (Complex 13)

In another embodiment, provided herein is a pharmaceutical composition for treatment and prevention of cancer/tumor. In certain embodiments, the method comprises induction of cell death, inhibition of cellular proliferation, inhibition of thioredoxin reductase and/or poisoning of thioredoxin reductase, and the inhibition of tumor growth in vivo. In one embodiment, the method comprises administering to a subject an effective amount of the Au(III)-NHC complexes. In one embodiment, the method comprises detecting physiological thiol-containing compounds including, but not limited to, cysteine (Cys), glutathione (GSH), dithiothreitol (DTT), with an effective amount of the Au(III)-NHC complexes. In one embodiment, the method comprises detecting fluorescence changes at proper wavelength. The Au(III)-NHC complex has a formula I, derivatives thereof; or a pharmaceutically acceptable salt, solvate, or hydrate thereof, wherein, X is a carbon atom;
Y is a nitrogen atom;
$R_3$, $R_4$ are each lone electron pairs;
$R_1$, $R_2$, $R_7$, $R_8$, $R_9$, $R_{10}$, $R_{11}$ are each —H;
$R_5$ is —$CH_3$;
$R_6$ is —$C_{16}^{14}H_{33}$;
n is +1, and
$yA^b$ is $CF_3SO_3^-$. (Complex 14)

In another embodiment, provided herein is a pharmaceutical composition for treatment and prevention of cancer/tumor. In certain embodiments, the method comprises induction of cell death, inhibition of cellular proliferation, inhibition of thioredoxin reductase and/or poisoning of thioredoxin reductase, and the inhibition of tumor growth in vivo. In one embodiment, the method comprises administering to a subject an effective amount of the Au(III)-NHC complexes. In one embodiment, the method comprises detecting physiological thiol-containing compounds including, but not limited to, cysteine (Cys), glutathione (GSH), dithiothreitol (DTT), with an effective amount of the Au(III)-NHC complexes. In one embodiment, the method comprises detecting fluorescence changes at proper wavelength. The Au(III)-NHC complex has a formula I, derivatives thereof; or a pharmaceutically acceptable salt, solvate, or hydrate thereof, wherein, X is a carbon atom;
Y is a nitrogen atom;
$R_3$, $R_4$ are each lone electron pairs;
$R_1$, $R_2$, $R_9$, $R_{10}$, $R_{11}$ are each —H;
$R_7$ and $R_8$ are joined together to form

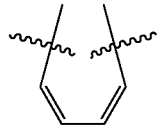 [SMILES: */C=C\C=C/*]

$R_5$, $R_6$ are each —$CH_3$;
n is +1, and
$yA^b$ is $CF_3SO_3^-$. (Complex 15)

5.1 Human Treatment

5.1.1 Formulations

The gold(III) complexes containing N-heterocyclic carbene ligand provided herein can be administered to a patient in the conventional form of preparations, such as injections and suspensions. Suitable formulations can be prepared by methods commonly employed using conventional, organic or inorganic additives, such as an excipient selected from fillers or diluents, binders, disintegrants, lubricants, flavoring agents, preservatives, stabilizers, suspending agents, dispersing agents, surfactants, antioxidants or solubilizers.

Excipients that may be selected are known to those skilled in the art and include, but are not limited to fillers or diluents (e.g., sucrose, starch, mannitol, sorbitol, lactose, glucose, cellulose, talc, calcium phosphate or calcium carbonate and the like), a binder (e.g., cellulose, carboxymethylcellulose, methylcellulose, hydroxymethylcellulose, hydroxypropylmethylcellulose, polypropylpyrrolidone, polyvinylpyrrolidone, gelatin, gum arabic, polyethyleneglycol or starch and the like), a disintegrants (e.g., sodium starch glycolate, croscarmellose sodium and the like), a lubricant (e.g., magnesium stearate, light anhydrous silicic acid, talc or sodium lauryl sulfate and the like), a flavoring agent (e.g., citric acid, or menthol and the like), a preservative (e.g., sodium benzoate, sodium bisulfite, methylparaben or propylparaben and the like), a stabilizer (e.g., citric acid, sodium citrate or acetic acid and the like), a suspending agent (e.g., methylcellulose, polyvinyl pyrrolidone or aluminum stearate and the like), a dispersing agent (e.g., hydroxypropylmethylcellulose and the like), surfactants (e.g., sodium lauryl sulfate, polaxamer, polysorbates and the like), antioxidants (e.g., ethylene diamine tetraacetic acid (EDTA), butylated hydroxyl toluene (BHT) and the like) and solubilizers (e.g., polyethylene glycols, SOLUTOL®, GELUCIRE® and the like). The effective amount of the gold(III) complexes containing N-heterocyclic carbene ligand provided herein in the pharmaceutical composition may be at a level that will exercise the desired effect.

In another embodiment, provided herein are compositions comprising an effective amount of gold(III) complexes containing N-heterocyclic carbene ligand provided herein and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

Compositions can be formulated to contain a daily dose, or a convenient fraction of a daily dose, in a dosage unit. In general, the composition is prepared according to known methods in pharmaceutical chemistry. Capsules can be prepared by mixing the gold (III) complexes containing N-heterocyclic carbene ligand provided herein with a suitable carrier or diluent and filling the proper amount of the mixture in capsules.

5.2 Method of Use

Solid tumor cancers that can be treated by the methods provided herein include, but are not limited to, sarcomas, carcinomas, and lymphomas. In specific embodiments, cancers that can be treated in accordance with the methods described include, but are not limited to, cancer of the breast, liver, neuroblastoma, head, neck, eye, mouth, throat, esophagus, esophagus, chest, bone, lung, kidney, colon, rectum or other gastrointestinal tract organs, stomach, spleen, skeletal muscle, subcutaneous tissue, prostate, breast, ovaries, testicles or other reproductive organs, skin, thyroid, blood, lymph nodes, kidney, liver, pancreas, and brain or central nervous system.

In particular embodiments, the methods for treating cancer provided herein inhibit, reduce, diminish, arrest, or stabilize a tumor associated with the cancer. In other embodiments, the methods for treating cancer provided herein inhibit, reduce, diminish, arrest, or stabilize the blood flow, metabolism, or edema in a tumor associated with the cancer or one or more symptoms thereof. In specific embodiments, the methods for treating cancer provided herein cause the regression of a tumor, tumor blood flow, tumor metabolism, or peritumor edema, and/or one or more symptoms associated with the cancer. In other embodiments, the methods for treating cancer provided herein maintain the size of the tumor so that it does not increase, or so that it increases by less than the increase of a tumor after administration of a standard therapy as measured by conventional methods available to one of skill in the art, such as digital rectal exam, ultrasound (e.g., transrectal ultrasound), CT Scan, MRI, dynamic contrast-enhanced MRI, or PET Scan. In specific embodiments, the methods for treating cancer provided herein decrease tumor size. In certain embodiments, the methods for treating cancer provided herein reduce the formation of a tumor. In certain embodiments, the methods for treating cancer provided herein eradicate, remove, or control primary, regional and/or metastatic tumors associated with the cancer. In some embodiments, the methods for treating cancer provided herein decrease the number or size of metastases associated with the cancer.

In certain embodiments, the methods for treating cancer provided herein reduce the tumor size (e.g., volume or diameter) in a subject by at least about 5%, 10%, 15%, 20%, 25%, 30%, 35%, 40%, 45%, 50%, 55%, 60%, 65%, 80%, 85%, 90%, 95%, 99%, or 100%, relative to tumor size (e.g., volume or diameter) prior to administration of gold(III) complexes containing N-heterocyclic carbene ligand as assessed by methods well known in the art, e.g., CT Scan, MRI, DCE-MRI, or PET Scan. In particular embodiments, the methods for treating cancer provided herein reduce the tumor volume or tumor size (e.g., diameter) in a subject by an amount in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor size (e.g., diameter) in a subject prior to administration of gold(III) complexes containing N-heterocyclic carbene ligand as assessed by methods well known in the art, e.g., CT Scan, MRI, DCE-MRI, or PET Scan.

In certain embodiments, the methods for treating cancer provided herein reduce the tumor perfusion in a subject by at least about 5%, 10%, 15%, 20%, 25%, 30%, 35%, 40%, 45%, 50%, 55%, 60%, 65%, 80%, 85%, 90%, 95%, 99%, or 100%, relative to tumor perfusion prior to administration of gold(III) complexes containing N-heterocyclic carbine ligand as assessed by methods well known in the art, e.g., MRI, DCE-MRI, or PET Scan. In particular embodiments, the methods for treating cancer provided herein reduce the tumor perfusion in a subject by an amount in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor perfusion prior to administration of gold(III) complexes containing N-heterocyclic carbene ligand, as assessed by methods well known in the art, e.g., MRI, DCE-MRI, or PET Scan.

In particular aspects, the methods for treating cancer provided herein inhibit or decrease tumor metabolism in a subject as assessed by methods well known in the art, e.g., PET scanning. In specific embodiments, the methods for treating cancer provided herein inhibit or decrease tumor metabolism in a subject by at least about 5%, 10%, 15%, 20%, 25%, 30%, 35%, 40%, 45%, 50%, 55%, 60%, 65%, 80%, 85%, 90%, 95%, or 100%, relative to tumor metabolism prior to administration of gold(III) complexes containing N-heterocyclic carbene ligand, as assessed by methods well known in the art, e.g., PET scanning. In particular embodiments, the methods for treating cancer provided herein inhibit or decrease tumor metabolism in a subject in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor metabolism prior to administration of gold(III) complexes containing N-heterocyclic carbene ligand, as assessed by methods well known in the art, e.g., PET scan.

5.3 Patient Population

In some embodiments, a subject treated for cancer in accordance with the methods provided herein is a human who has or is diagnosed with cancer. In other embodiments, a subject treated for cancer in accordance with the methods provided herein is a human predisposed or susceptible to cancer. In some embodiments, a subject treated for cancer in accordance with the methods provided herein is a human at risk of developing cancer.

In one embodiment, a subject treated for cancer in accordance with the methods provided herein is a human infant. In another embodiment, a subject treated for cancer in accordance with the methods provided herein is a human toddler. In another embodiment, a subject treated for cancer in accordance with the methods provided herein is a human child. In another embodiment, a subject treated for cancer in accordance with the methods provided herein is a human adult. In another embodiment, a subject treated for cancer in accordance with the methods provided herein is a middle-aged human. In another embodiment, a subject treated for cancer in accordance with the methods provided herein is an elderly human.

In certain embodiments, a subject treated for cancer in accordance with the methods provided herein has a cancer that metastasized to other areas of the body, such as the bones, lung and liver. In certain embodiments, a subject treated for cancer in accordance with the methods provided herein is in remission from the cancer. In some embodiments, a subject treated for cancer in accordance with the methods provided herein that has a recurrence of the cancer. In certain embodiments, a subject treated in accordance with the methods provided herein is experiencing recurrence of one or more tumors associated with cancer.

In certain embodiments, a subject treated for cancer in accordance with the methods provided herein is a human that is about 1 to about 5 years old, about 5 to 10 years old, about 10 to about 18 years old, about 18 to about 30 years old, about 25 to about 35 years old, about 35 to about 45 years old, about 40 to about 55 years old, about 50 to about 65 years old, about 60 to about 75 years old, about 70 to about 85 years old, about 80 to about 90 years old, about 90 to about 95 years old or about 95 to about 100 years old, or any age in between. In a specific embodiment, a subject treated for cancer in accordance with the methods provided herein is a human that is 18 years old or older. In a particular embodiment, a subject treated for cancer in accordance with the methods provided herein is a human child that is between the age of 1 year old to 18 years old. In a certain embodiment, a subject treated for cancer in accordance with the methods provided herein is a human that is between the age of 12 years old and 18 years old. In a certain embodiment, the subject is a male human. In another embodiment, the subject is a female human. In one embodiment, the subject is a female human that is not pregnant or is not breastfeeding. In one embodiment, the subject is a female that is pregnant or will/might become pregnant, or is breast feeding.

In some embodiments, a subject treated for cancer in accordance with the methods provided herein is administered gold (III) complexes containing N-heterocyclic carbene ligand or a pharmaceutical composition thereof, or a combination therapy before any adverse effects or intolerance to therapies other than the gold(III) complexes containing N-heterocyclic carbene ligand develops. In some embodiments, a subject treated for cancer in accordance with the methods provided herein is a refractory patient. In a certain embodiment, a refractory patient is a patient refractory to a standard therapy (e.g., surgery, radiation, anti-androgen therapy and/or drug therapy such as chemotherapy). In certain embodiments, a patient with cancer is refractory to a therapy when the cancer has not significantly been eradicated and/or the one or more symptoms have not been significantly alleviated. The determination of whether a patient is refractory can be made either in vivo or in vitro by any method known in the art for assaying the effectiveness of a treatment of cancer, using art-accepted meanings of "refractory" in such a context. In various embodiments, a patient with cancer is refractory when one or more tumors associated with cancer, have not decreased or have increased. In various embodiments, a patient with cancer is refractory when one or more tumors metastasize and/or spread to another organ.

In some embodiments, a subject treated for cancer accordance with the methods provided herein is a human that has proven refractory to therapies other than treatment with gold (III) complexes containing N-heterocyclic carbene ligand, but is no longer on these therapies. In certain embodiments, a subject treated for cancer in accordance with the methods provided herein is a human already receiving one or more conventional anti-cancer therapies, such as surgery, drug therapy such as chemotherapy, anti-androgen therapy or radiation. Among these patients are refractory patients, patients who are too young for conventional therapies, and patients with recurring tumors despite treatment with existing therapies.

5.4 Dosage

In one aspect, a method for treating cancer presented herein involves the administration of a unit dosage of gold(III) complexes containing N-heterocyclic carbene ligand thereof. The dosage may be administered as often as determined effective (e.g., once, twice or three times per day, every other day, once or twice per week, biweekly or monthly). In certain embodiments, a method for treating cancer presented herein involves the administration to a subject in need thereof of a unit dose of gold(III) complexes containing N-heterocyclic carbene ligand that can be determined by one skilled in the art.

In some embodiments, a unit dose of gold(III) complexes containing N-heterocyclic carbene ligand or a pharmaceutical composition thereof is administered to a subject once per day, twice per day, three times per day; once, twice or three times every other day (i.e., on alternate days); once, twice or three times every two days; once, twice or three times every three days; once, twice or three times every four days; once, twice or three times every five days; once, twice, or three times once a week, biweekly or monthly, and the dosage may be administered orally.

5.5 Combination Therapy

Presented herein are combination therapies for the treatment of cancer which involve the administration of gold(III) complexes containing N-heterocyclic carbene ligand in combination with one or more additional therapies to a subject in need thereof. In a specific embodiment, presented herein are combination therapies for the treatment of cancer which involve the administration of an effective amount of gold(III) complexes containing N-heterocyclic carbene ligand in combination with an effective amount of another therapy to a subject in need thereof.

As used herein, the term "in combination," refers, in the context of the administration of gold(III) complexes containing N-heterocyclic carbene ligand, to the administration of gold(III) complexes containing N-heterocyclic carbene ligand prior to, concurrently with, or subsequent to the administration of one or more additional therapies (e.g., agents, surgery, or radiation) for use in treating cancer. The use of the term "in combination" does not restrict the order in which gold(III) complexes containing N-heterocyclic carbene ligand and one or more additional therapies are administered to a subject. In specific embodiments, the interval of time between the administration of gold(III) complexes containing N-heterocyclic carbene ligand and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain embodiments, gold(III) complexes containing N-heterocyclic carbene ligand and one or more additional therapies are administered less than 1 day, 1 week, 2 weeks, 3 weeks, 4 weeks, one month, 2 months, 3 months, 6 months, 1 year, 2 years, or 5 years apart.

In some embodiments, the combination therapies provided herein involve administering gold(III) complexes containing N-heterocyclic carbene ligand daily, and administering one or more additional therapies once a week, once every 2 weeks, once every 3 weeks, once every 4 weeks, once every month, once every 2 months (e.g., approximately 8 weeks), once every 3 months (e.g., approximately 12 weeks), or once every 4 months (e.g., approximately 16 weeks). In certain embodiments, gold(III) complexes containing N-heterocyclic carbene ligand and one or more additional therapies are cyclically administered to a subject. Cycling therapy involves the administration of gold(III) complexes containing N-heterocyclic carbene ligand for a period of time, followed by the administration of one or more additional therapies for a period of time, and repeating this sequential administration. In certain embodiments, cycling therapy may also include a period of rest where gold(III) complexes containing N-heterocyclic carbene ligand or the additional therapy is not administered for a period of time (e.g., 2 days, 3 days, 4 days, 5 days, 6 days, 7 days, 1 week, 2 weeks, 3 weeks, 4 weeks, 5 weeks, 10 weeks, 20 weeks, 1 month, 2 months, 3 months, 4 months, 5 months, 6 months, 7 months, 8 months, 9 months, 10 months, 11 months, 12 months, 2 years, or 3 years). In an embodiment, the number of cycles administered is from 1 to 12 cycles, from 2 to 10 cycles, or from 2 to 8 cycles.

In some embodiments, the methods for treating cancer provided herein comprise administering gold(III) complexes containing N-heterocyclic carbene ligand as a single agent for a period of time prior to administering the gold(III) complexes containing N-heterocyclic carbene ligand in combination with an additional therapy. In certain embodiments, the methods for treating cancer provided herein comprise administering an additional therapy alone for a period of time prior to administering gold(III) complexes containing N-heterocyclic carbene ligand in combination with the additional therapy.

In some embodiments, the administration of gold(III) complexes containing N-heterocyclic carbene ligand and one or more additional therapies in accordance with the methods presented herein have an additive effect relative the administration of gold(III) complexes containing N-heterocyclic carbene ligand or said one or more additional therapies alone. In some embodiments, the administration of gold(III) complexes containing N-heterocyclic carbene ligand and one or more additional therapies in accordance with the methods presented herein have a synergistic effect relative to the administration of the Compound or said one or more additional therapies alone.

As used herein, the term "synergistic," refers to the effect of the administration of gold(III) complexes containing N-heterocyclic carbene ligand in combination with one or more additional therapies (e.g., agents), which combination is more effective than the additive effects of any two or more single therapies (e.g., agents). In a specific embodiment, a synergistic effect of a combination therapy permits the use of lower dosages (e.g., sub-optimal doses) of gold(III) complexes containing N-heterocyclic carbene ligand or an additional therapy and/or less frequent administration of gold(III) complexes containing N-heterocyclic carbene ligand or an additional therapy to a subject. In certain embodiments, the ability to utilize lower dosages of gold(III) complexes containing N-heterocyclic carbene ligand or of an additional therapy and/or to administer gold(III) complexes containing N-heterocyclic carbene ligand or said additional therapy less frequently reduces the toxicity associated with the administration of gold(III) complexes containing N-heterocyclic carbene ligand or of said additional therapy, respectively, to a subject without reducing the efficacy of gold(III) complexes containing N-heterocyclic carbene ligand or of said additional therapy, respectively, in the treatment of cancer. In some embodiments, a synergistic effect results in improved efficacy of gold(III) complexes containing N-heterocyclic carbene ligand and each of said additional therapies in treating cancer. In some embodiments, a synergistic effect of a combination of gold(III) complexes containing N-heterocyclic carbene ligand and one or more additional therapies avoids or reduces adverse or unwanted side effects associated with the use of any single therapy.

The combination of gold(III) complexes containing N-heterocyclic carbene ligand and one or more additional therapies can be administered to a subject in the same pharmaceutical composition. Alternatively, gold(III) complexes containing N-heterocyclic carbene ligand and one or more additional therapies can be administered concurrently to a subject in separate pharmaceutical compositions. Gold(III) complexes containing N-heterocyclic carbene ligand and one or more additional therapies can be administered sequentially to a subject in separate pharmaceutical compositions. Gold(III) complexes containing N-heterocyclic carbene ligand and one or more additional therapies may also be administered to a subject by the same or different routes of administration.

The combination therapies provided herein involve administering to a subject in need thereof gold(III) complexes containing N-heterocyclic carbene ligand in combination with conventional, or known, therapies for treating cancer. Other therapies for cancer or a condition associated therewith are aimed at controlling or relieving one or more symptoms. Accordingly, in some embodiments, the combination therapies provided herein involve administering to a subject to in need thereof a pain reliever, or other therapies aimed at alleviating or controlling one or more symptoms associated with or a condition associated therewith.

Specific examples of anti-cancer agents that may be used in combination with gold(III) complexes containing N-heterocyclic carbene ligand include: a hormonal agent (e.g., aromatase inhibitor, selective estrogen receptor modulator (SERM), and estrogen receptor antagonist), chemotherapeutic agent (e.g., microtubule dissembly blocker, antimetabolite, topisomerase inhibitor, and DNA crosslinker or damaging agent), anti-angiogenic agent (e.g., VEGF antagonist, receptor antagonist, integrin antagonist, vascular targeting agent (VTA)/vascular disrupting agent (VDA)), radiation therapy, and conventional surgery.

Non-limiting examples of hormonal agents that may be used in combination with gold(III) complexes containing N-heterocyclic carbene ligand include aromatase inhibitors, SERMs, and estrogen receptor antagonists. Hormonal agents that are aromatase inhibitors may be steroidal or nonsteroidal. Non-limiting examples of nonsteroidal hormonal agents include letrozole, anastrozole, aminoglutethimide, fadrozole, and vorozole. Non-limiting examples of steroidal hormonal agents include aromasin (exemestane), formestane, and testolactone. Non-limiting examples of hormonal agents that are SERMs include tamoxifen (branded/marketed as Nolvadex®), afimoxifene, arzoxifene, bazedoxifene, clomifene, femarelle, lasofoxifene, ormeloxifene, raloxifene, and toremifene. Non-limiting examples of hormonal agents that are estrogen receptor antagonists include fulvestrant. Other hormonal agents include but are not limited to abiraterone and lonaprisan.

Non-limiting examples of chemotherapeutic agents that may be used in combination with gold(III) complexes containing N-heterocyclic carbene ligand include microtubule disassembly blocker, antimetabolite, topisomerase inhibitor, and DNA crosslinker or damaging agent. Chemotherapeutic agents that are microtubule dissemby blockers include, but are not limited to, taxenes (e.g., paclitaxel (branded/marketed as TAXOL®), docetaxel, abraxane, larotaxel, ortataxel, and tesetaxel); epothilones (e.g., ixabepilone); and vinca alkaloids (e.g., vinorelbine, vinblastine, vindesine, and vincristine (branded/marketed as ONCOVIN®)).

Chemotherapeutic agents that are antimetabolites include, but are not limited to, folate anitmetabolites (e.g., methotrexate, aminopterin, pemetrexed, raltitrexed); purine antimetabolites (e.g., cladribine, clofarabine, fludarabine, mercaptopurine, pentostatin, thioguanine); pyrimidine antimetabolites (e.g., 5-fluorouracil, capcitabine, gemcitabine (GEMZAR®), cytarabine, decitabine, floxuridine, tegafur); and deoxyribonucleotide antimetabolites (e.g., hydroxyurea).

Chemotherapeutic agents that are topoisomerase inhibitors include, but are not limited to, class I (camptotheca) topoisomerase inhibitors (e.g., topotecan (branded/marketed as HYCAMTIN®) irinotecan, rubitecan, and belotecan); class II (podophyllum) topoisomerase inhibitors (e.g., etoposide or VP-16, and teniposide); anthracyclines (e.g., doxorubicin, epirubicin, Doxil, aclarubicin, amrubicin, daunorubicin, idarubicin, pirarubicin, valrubicin, and zorubicin); and anthracenediones (e.g., mitoxantrone, and pixantrone).

Chemotherapeutic agents that are DNA crosslinkers (or DNA damaging agents) include, but are not limited to, alkylating agents (e.g., cyclophosphamide, mechlorethamine, ifosfamide (branded/marketed as IFEX®), trofosfamide, chlorambucil, melphalan, prednimustine, bendamustine, uramustine, estramustine, carmustine (branded/marketed as BiCNU®), lomustine, semustine, fotemustine, nimustine, ranimustine, streptozocin, busulfan, mannosulfan, treosulfan, carboquone, N,N'N'-triethylenethiophosphoramide, triaziquone, triethylenemelamine); alkylating-like agents (e.g., carboplatin (branded/marketed as PARAPLATIN®), cisplatin, oxaliplatin, nedaplatin, triplatin tetranitrate, satraplatin, picoplatin); nonclassical DNA crosslinkers (e.g., procarbazine, dacarbazine, temozolomide (branded/marketed as TEMODAR®), altretamine, mitobronitol); and intercalating agents (e.g., actinomycin, bleomycin, mitomycin, and plicamycin).

Non-limiting examples of other therapies that may be administered to a subject in combination with gold(III) complexes containing N-heterocyclic carbene ligand include:

(1) a statin such as lovostatin (e.g., branded/marketed as) MEVACOR®);

(2) an mTOR inhibitor such as sirolimus which is also known as Rapamycin (e.g., branded/marketed as RAPAMUNE®), temsirolimus (e.g., branded/marketed as TORISEL®), evorolimus (e.g., branded/marketed as) AFINITOR®), and deforolimus;

(3) a farnesyltransferase inhibitor agent such as tipifarnib;

(4) an antifibrotic agent such as pirfenidone;

(5) a pegylated interferon such as PEG-interferon alfa-2b;

(6) a CNS stimulant such as methylphenidate (branded/marketed as RITALIN®);

(7) a HER-2 antagonist such as anti-HER-2 antibody (e.g., trastuzumab) and kinase inhibitor (e.g., lapatinib);

(8) an IGF-1 antagonist such as an anti-IGF-1 antibody (e.g., AVE1642 and IMC-A11) or an IGF-1 kinase inhibitor;

(9) EGFR/HER-1 antagonist such as an anti-EGFR antibody (e.g., cetuximab, panitumamab) or EGFR kinase inhibitor (e.g., erlotinib; gefitinib);

(10) SRC antagonist such as bosutinib;

(11) cyclin dependent kinase (CDK) inhibitor such as seliciclib;

(12) Janus kinase 2 inhibitor such as lestaurtinib;

(13) proteasome inhibitor such as bortezomib;

(14) phosphodiesterase inhibitor such as anagrelide;

(15) inosine monophosphate dehydrogenase inhibitor such as tiazofurine;

(16) lipoxygenase inhibitor such as masoprocol;

(17) endothelin antagonist;

(18) retinoid receptor antagonist such as tretinoin or alitretinoin;

(19) immune modulator such as lenalidomide, pomalidomide, or thalidomide;

(20) kinase (e.g., tyrosine kinase) inhibitor such as imatinib, dasatinib, erlotinib, nilotinib, gefitinib, sorafenib, sunitinib, lapatinib, or TG100801;

(21) non-steroidal anti-inflammatory agent such as celecoxib (branded/marketed as CELEBREX®);

(22) human granulocyte colony-stimulating factor (G-CSF) such as filgrastim (branded/marketed as NEUPOGEN®);

(23) folinic acid or leucovorin calcium;

(24) integrin antagonist such as an integrin α5β1-antagonist (e.g., JSM6427);

(25) nuclear factor kappa beta (NF-κβ) antagonist such as OT-551, which is also an anti-oxidant;

(26) hedgehog inhibitor such as CUR61414, cyclopamine, GDC-0449, and anti-hedgehog antibody;

(27) histone deacetylase (HDAC) inhibitor such as SAHA (also known as vorinostat (branded/marketed as ZOLINZA)), PCI-24781, SB939, CHR-3996, CRA-024781, ITF2357, JNJ-26481585, or PCI-24781;

(28) retinoid such as isotretinoin (e.g., branded/marketed as ACCUTANE®);

(29) hepatocyte growth factor/scatter factor (HGF/SF) antagonist such as HGF/SF monoclonal antibody (e.g., AMG 102);

(30) synthetic chemical such as antineoplaston;

(31) anti-diabetic such as rosaiglitazone (e.g., branded/marketed as AVANDIA®);

(32) antimalarial and amebicidal drug such as chloroquine (e.g., branded/marketed as ARALEN®);

(33) synthetic bradykinin such as RMP-7;

(34) platelet-derived growth factor receptor inhibitor such as SU-101;

(35) receptor tyrosine kinase inhibitorsof Flk-1/KDR/VEGFR2, FGFR1 and PDGFR beta such as SU5416 and SU6668;

(36) anti-inflammatory agent such as sulfasalazine (e.g., branded/marketed as AZULFIDINE®); and

(37) TGF-beta antisense therapy.

6. EXAMPLES

Example 6.1

Preparation and Characterization of the Au(III)-NHC Complexes

Example 1 illustrates the synthesis and characterization of the gold(III) complexes bearing N-heterocyclic carbene complexes.

PPP-Au—Cl was synthesized similar to a reported procedure [Acta Cryst. (2010). E66,m64].

Synthesis of IPI-Au—Cl

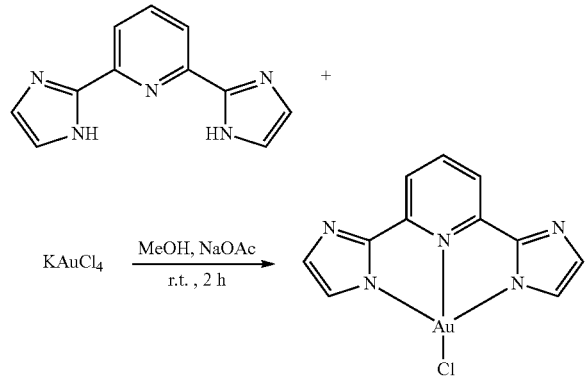

A mixture of H$_2$IPI (251.5 mg, 1.19 mmol), KAuCl$_4$ (300 mg, 0.794 mmol), and sodium acetate (325 mg, 3.97 mmol) was stirred in methanol (10 mL) at room temperature; red solid appeared in several seconds. After 2 h, the product was filtered and washed with methanol and then with diethyl ether. Yield 90%; $^1$H NMR (400 MHz, DMSO-d$_6$, 25° C.): δ=8.22 (t, J=7.9 Hz, 1 H), 7.63 (d, J=7.9 Hz, 2 H), 7.33 (d, J=0.72 Hz, 2 H), 7.31 (d, J=0.70 Hz, 2 H); FAB-MS: m/z 442 [M+1]$^+$; Elemental analysis calcd (%) for C$_{11}$H$_7$AuClN$_5$: C, 29.92; H, 1.60; N, 15.86; found: C, 30.19; H, 1.77; N, 15.71.

Synthesis of BPB-Au—Cl

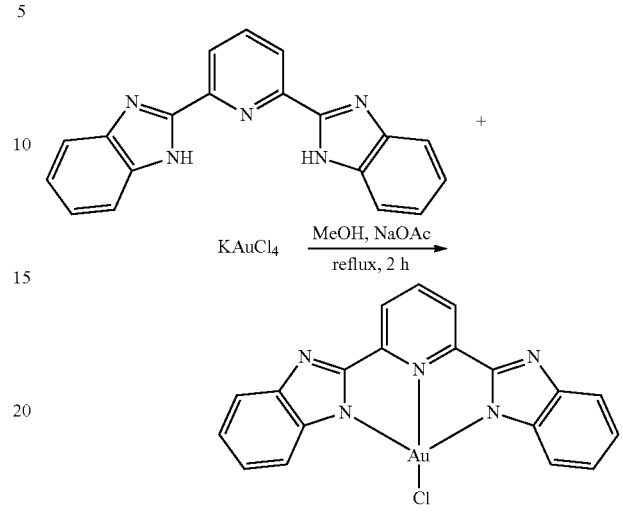

A mixture of H$_2$BPB (165 mg, 0.53 mmol), KAuCl$_4$ (300 mg, 0.794 mmol), and sodium acetate (325 mg, 3.97 mmol) in methanol (25 mL) was heated to reflux for 2 h. The product was filtered and washed with methanol and then with diethyl ether. Yield 95%; $^1$H NMR (400 MHz, DMSO-d$_6$, 25° C.): δ=8.51 (t, J=7.9 Hz, 1H), 8.18 (d, J=7.9 Hz, 2H), 8.14 (d, J=8.1 Hz, 2H), 7.78 (d, J=8.0 Hz, 2H), 7.37 (m, 2H), 7.28 (m, 2H); FAB-MS: m/z 542 [M+1]$^+$; Elemental analyses calcd (%) for C$_{19}$H$_{11}$AuClN$_5$.H$_2$O: C, 40.77; H, 2.34; N, 12.51. found: C, 40.29; H, 2.18; N, 12.39.

Synthesis of 1

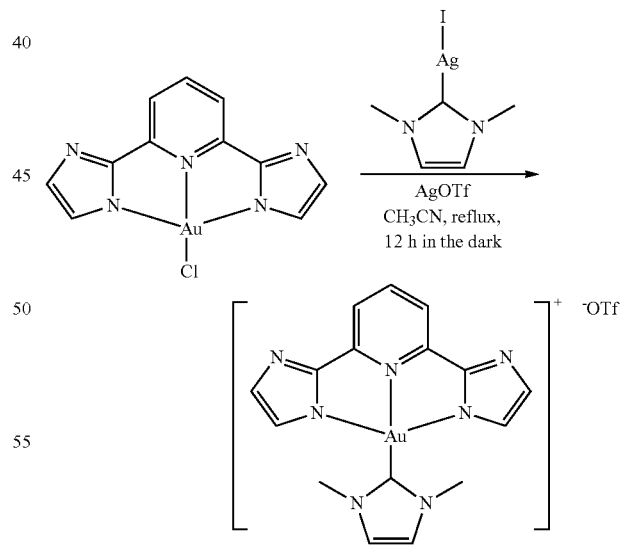

A mixture of IPI-Au—Cl (80 mg, 0.181 mmol), silver triflate (55.7 mg, 0.217 mmol), and (1,3-dimethyl-1H-imidazol-2(3H)-ylidene)silver(I) iodide (71.9 mg, 0.217 mmol) in acetonitrile (10 mL) was heated to reflux for 12 h in the dark. After cooling to room temperature, the reaction mixture was filtered, and the filtrate was purified by alumina with CH$_3$CN/CH$_2$Cl$_2$ as eluents, and yellow powder was obtained. Yield 45%; $^1$H NMR (300 MHz, CD$_3$CN, 25° C.): δ=8.24 (t, J=7.9 Hz, 1H), 7.72 (d, J=8.0 Hz, 2H), 7.57 (s, 2H), 7.25 (d, J=0.9 Hz, 2H), 7.01 (d, J=0.9 Hz, 2H), 3.93 (s, 6H); FAB-MS: m/z 502 [M−OTf]$^+$; Elemental analyses calcd (%) for C$_{17}$H$_{15}$AuF$_3$N$_7$O$_3$S: C, 31.35; H, 2.32; N, 15.05; found: C, 31.51; H, 2.45; N, 15.22.

Synthesis of 2

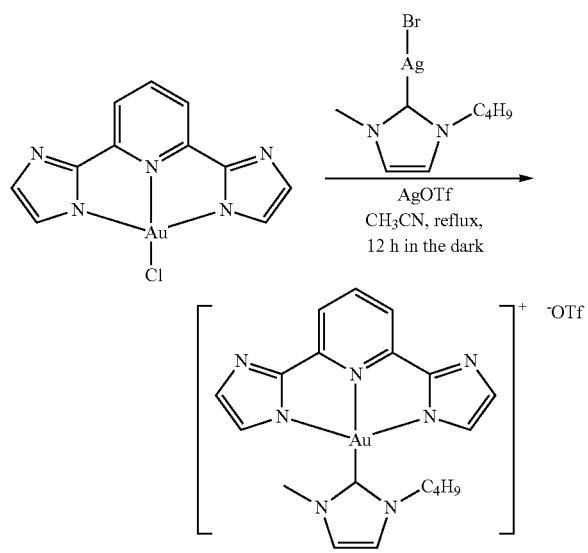

The procedure is similar to that for 1. Yield 60%; $^1$H NMR (400 MHz, CD$_3$CN, 25° C.): δ=8.24 (t, J=8.0 Hz, 1H), 7.72 (d, J=8.0 Hz, 2H), 7.62 (d, J=2.1 Hz, 1H), 7.59 (d, J=2.1 Hz, 1H), 7.25 (d, J=0.9 Hz, 2H), 6.98 (d, J=0.9 Hz, 2H), 4.25 (t, J=7.3 Hz, 2H), 3.93 (s, 3H), 1.78 (m, 2H), 1.24 (m, 2H), 0.81 (t, J=7.4 Hz, 3H); FAB-MS: m/z 544 [M−OTf]$^+$; Elemental analysis calcd (%) for C$_{20}$H$_{21}$AuF$_3$N$_7$O$_3$S.H$_2$O: C, 33.76; H, 3.26; N, 13.78; found: C, 33.87; H, 3.24; N, 13.87.

Synthesis of 3

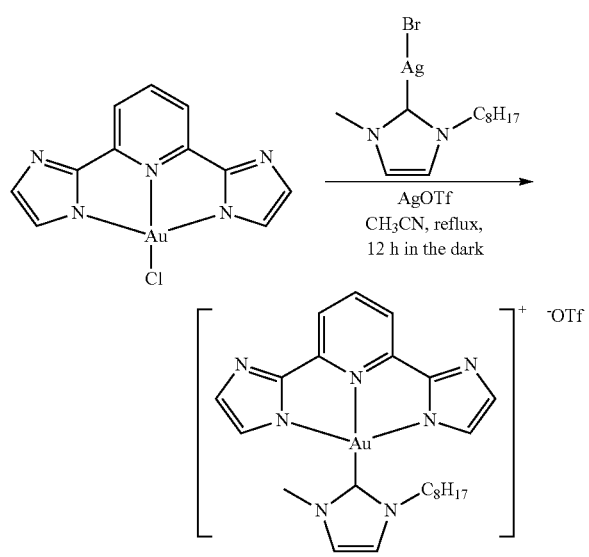

The procedure is similar to that for 1. Yield 45%; $^1$H NMR (400 MHz, CD$_3$CN, 25° C.): δ=8.23 (t, J=8.0 Hz, 1H), 7.71 (d, J=8.0 Hz, 2H), 7.62 (d, J=2.1 Hz, 1H), 7.60 (d, J=2.1 Hz, 1H), 7.25 (d, J=0.9 Hz, 2H), 6.99 (d, J=0.9 Hz, 2H), 4.26 (t, J=7.1 Hz, 2H), 3.94 (s, 3H), 1.80 (m, 2H), 1.17 (m, 6H), 1.11 (m, 4H), 0.82 (t, J=7.2 Hz, 3H); FAB-MS: m/z 600 [M−OTf]$^+$; Elemental analysis calcd (%) for C$_{24}$H$_{29}$AuF$_3$N$_7$O$_3$S: C, 38.46; H, 3.90; N, 13.08; found: C, 38.45; H, 3.99; N, 13.00.

Synthesis of 4

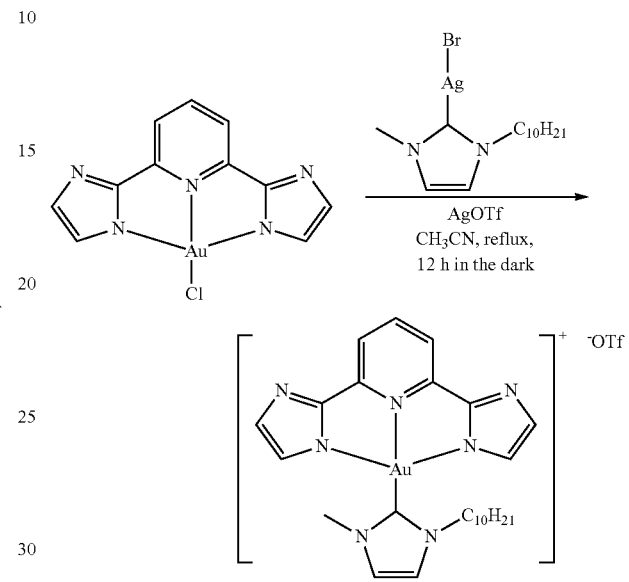

The procedure is similar to that for 1. Yield 48%; $^1$H NMR (300 MHz, CD$_3$CN, 25° C.): δ=8.24 (t, J=8.0 Hz, 1H), 7.72 (d, J=7.9 Hz, 2H), 7.62 (d, J=2.7 Hz, 1H), 7.59 (d, J=2.7 Hz, 1H), 7.25 (d, J=0.9 Hz, 2H), 6.99 (d, J=0.9 Hz, 2H), 4.25 (t, J=7.1 Hz, 2H), 3.93 (s, 3H), 1.82 (m, 2H), 1.27-1.10 (m, 14H), 0.85 (t, J=6.9 Hz, 3H); FAB-MS: m/z 628 [M−OTf]$^+$; Elemental analysis calcd (%) for C$_{26}$H$_{33}$AuF$_3$N$_7$O$_3$S: C, 40.16; H, 4.28; N, 12.61; found: C, 40.28, H, 4.42, N, 12.78.

Synthesis of 5

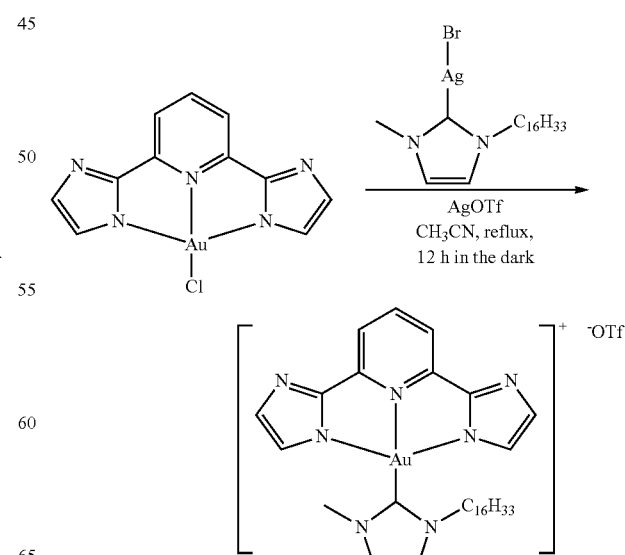

The procedure is similar to that for 1. Yield 45%; $^1$H NMR (300 MHz, CD$_3$CN, 25° C.): δ=8.23 (t, J=8.0 Hz, 1H), 7.72 (d, J=8.0 Hz, 2H), 7.63 (d, J=2.0 Hz, 1H), 7.61 (d, J=2.0 Hz, 1H), 7.23 (d, J=0.9 Hz, 2H), 6.99 (d, J=0.9 Hz, 2H), 4.26 (t, J=7.1 Hz, 2H), 3.94 (s, 3H), 1.80 (m, 2H), 1.17-1.32 (m, 26H), 0.87 (t, J=7.2 Hz, 3H); FAB-MS: m/z 712 [M−OTf]$^+$; Elemental analysis calcd (%) for C$_{32}$H$_{45}$AuF$_3$N$_7$O$_3$S.H$_2$O: C, 43.69; H, 5.38; N, 11.14; found: C, 44.00; H, 5.50; N, 11.16.

Synthesis of 6

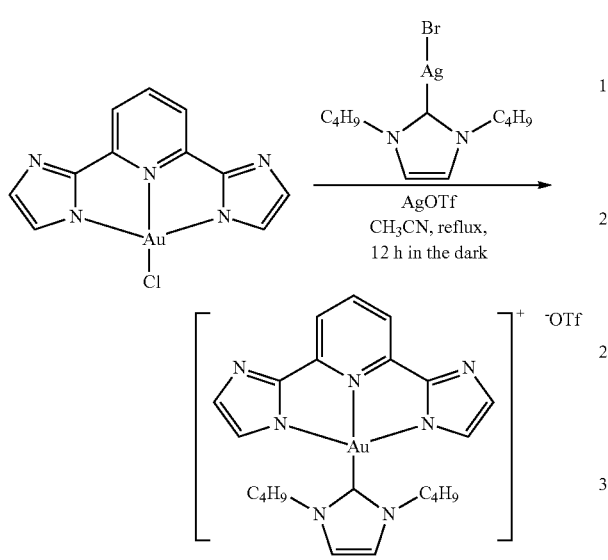

Synthesis of 7

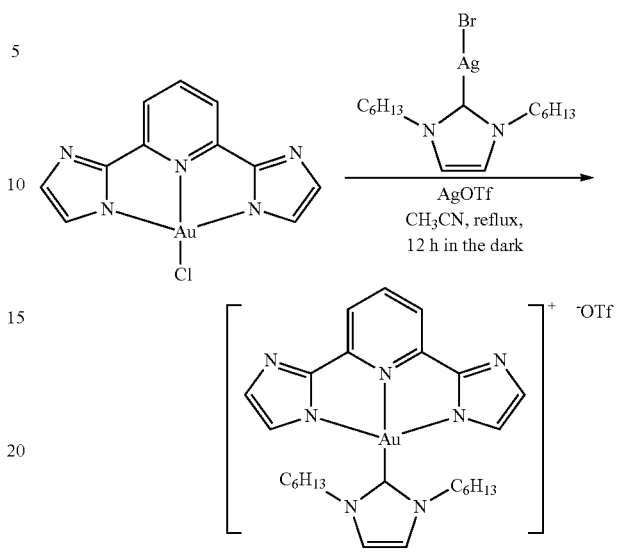

The procedure is similar to that for 1. Yield 55%; $^1$H NMR (400 MHz, CD$_3$CN, 25° C.): δ=8.24 (t, J=8.0 Hz, 1H), 7.72 (d, J=8.0 Hz, 2H), 7.65 (s, 2H), 7.24 (d, J=0.8 Hz, 2H), 6.96 (d, J=0.8 Hz, 2H), 4.26 (t, J=7.2 Hz, 4H), 1.79 (m, 4H), 1.20-1.15 (m, 12H), 0.76 (t, J=6.9 Hz, 6H); FAB-MS: m/z 642 [M−OTf]$^+$; Elemental Analysis calcd (%) for C$_{27}$H$_{35}$AuF$_3$N$_7$O$_3$S: C, 40.96; H, 4.46; N, 12.39; found: C, 41.26; H, 4.51; N, 12.48.

Synthesis of 8

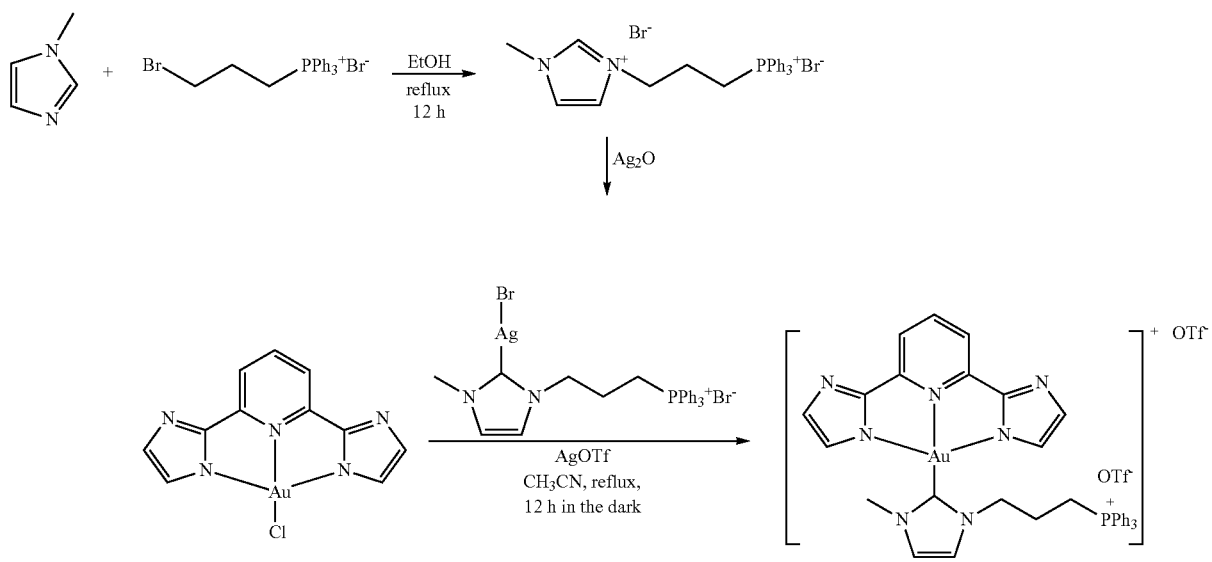

The procedure is similar to that for 1. Yield 52%; $^1$H NMR (400 MHz, CD$_3$CN, 25° C.): δ=8.23 (t, J=7.9 Hz, 1H), 7.71 (d, J=8.0 Hz, 2H), 7.66 (s, 2H), 7.24 (d, J=1.0 Hz, 2H), 6.95 (d, J=1.0 Hz, 2H), 4.28 (t, J=7.3 Hz, 4H), 1.79 (m, 4H), 1.25 (m, 4H), 0.81 (t, J=7.4 Hz, 6H); FAB-MS: m/z 586 [M−OTf]$^+$; Elemental Analysis calcd (%) for C$_{23}$H$_{27}$AuF$_3$N$_7$O$_3$S: C, 37.56; H, 3.70; N, 13.33; found: C, 38.04; H, 3.92; N, 13.09.

1-Methyl-3-(3-(triphenylphosphonio)propyl)-1H-imidazol-3-ium bromide was synthesized by refluxing the mixture of 1-methyl-1H-imidazole and (3-bromopropyl)triphenylphosphonium bromide (1:1) in ethanol for 12 h; after cooling down, the solvent was removed and the crude product was washed with ethyl acetate. Then the white product was treated with silver (I) oxide in CH$_2$Cl$_2$ for 12 h, and the crude Ag—NHC product was filtered and washed with CH$_2$Cl$_2$ and then with diethyl ether, and was used for the next step directly. The procedure for the synthesis of 3 is similar to that for 1. Total yield 32%; ¹H NMR (400 MHz, CD₃CN, 25° C.): δ=8.21 (t, J=8.0 Hz, 1H), 7.82 (m, 3H), 7.69-7.72 (m, 3H), 7.66 (d, J=2.0 Hz, 1H), 7.55-7.63 (m, 12H), 7.17 (d, J=0.9 Hz, 2H), 6.98 (d, J=0.9 Hz, 2H), 4.57 (t, J=7.1 Hz, 2H), 3.94 (s, 3H), 3.27 (m, 2H), 2.11 (m, 2H); FAB-MS: m/z 940 [M−OTf]⁺; Elemental Analysis calcd (%) for $C_{38}H_{33}AuF_6N_7O_6PS_2 \cdot H_2O$: C, 41.20; H, 3.18; N, 8.85; found: C, 41.25; H, 3.29; N, 8.72.

Synthesis of 9

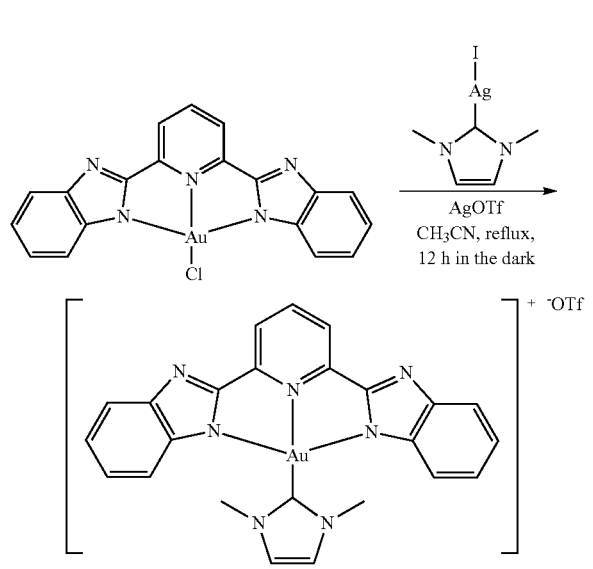

The procedure is similar to that for 1. Yield 43%; ¹H NMR (400 MHz, CD₃CN, 25° C.): δ=8.51 (t, J=7.9 Hz, 1H), 8.24 (d, J=7.9 Hz, 2H), 7.85 (s, 2H), 7.80 (d, J=8.2 Hz, 2H), 7.31-7.23 (m, 4H), 5.99 (d, J=7.9 Hz, 2H), 4.01 (s, 6H); FAB-MS: m/z 602 [M−OTf]⁺; Elemental Analysis calcd (%) for $C_{25}H_{19}AuF_3N_7O_3S \cdot H_2O \cdot CH_2Cl_2$: C, 36.55; H, 2.71; N, 11.48; found: C, 36.46; H, 2.57; N, 11.34.

Synthesis of 10

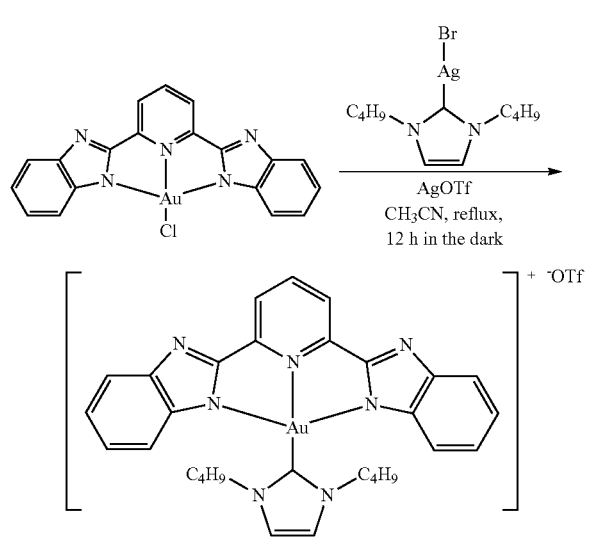

The procedure is similar to that for 1. Yield 51%; ¹H NMR (300 MHz, CD₃CN, 25° C.): δ=8.49 (t, J=7.9 Hz, 1H), 8.24 (d, J=7.9 Hz, 2H), 7.92 (s, 2H), 7.80 (d, J=7.4 Hz, 2H), 7.31-7.20 (m, 4H), 5.91 (d, J=8.6 Hz, 2H), 4.35 (t, J=7.3 Hz, 4H), 1.71 (m, 4H), 1.24 (m, 4H), 0.59 (t, J=7.3 Hz, 6H); FAB-MS: m/z 686 [M−OTf]⁺; Elemental Analysis calcd (%) for $C_{31}H_{31}AuF_3N_7O_3S$: C, 44.56; H, 3.74; N, 11.73; found: C, 44.16; H, 3.84; N, 11.62.

Synthesis of 11

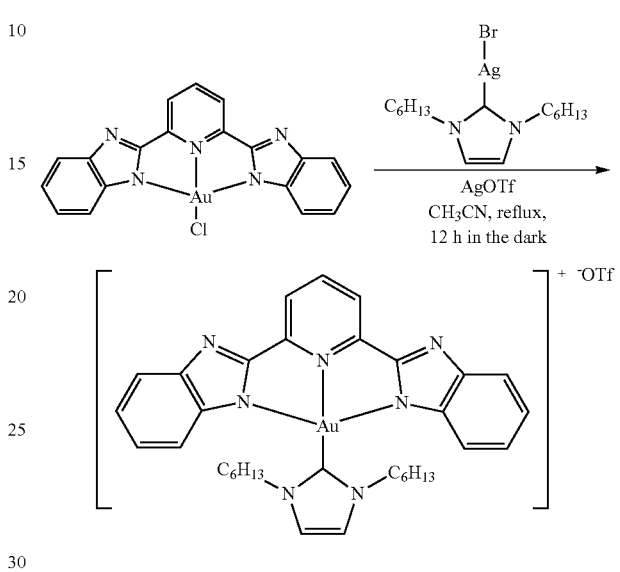

The procedure is similar to that for 1. Yield 55%; ¹H NMR (300 MHz, CD₃CN, 25° C.): δ=8.50 (t, J=7.9 Hz, 1H), 8.24 (d, J=8.0 Hz, 2H), 7.93 (s, 2H), 7.80 (d, J=7.5 Hz, 2H), 7.31-7.20 (m, 4H), 5.93 (d, J=7.0 Hz, 2H), 4.35 (t, J=7.2 Hz, 4H), 1.73 (m, 4H), 1.15 (m, 4H), 0.89 (m, 8H), 0.56 (t, J=7.1 Hz, 6H); FAB-MS: m/z 742 [M−OTf]⁺; Elemental Analysis calcd (%) for $C_{35}H_{39}AuF_3N_7O_3S$: C, 47.14; H, 4.41; N, 10.99; found: C, 47.00, H, 4.46, N, 10.78.

Synthesis of 12

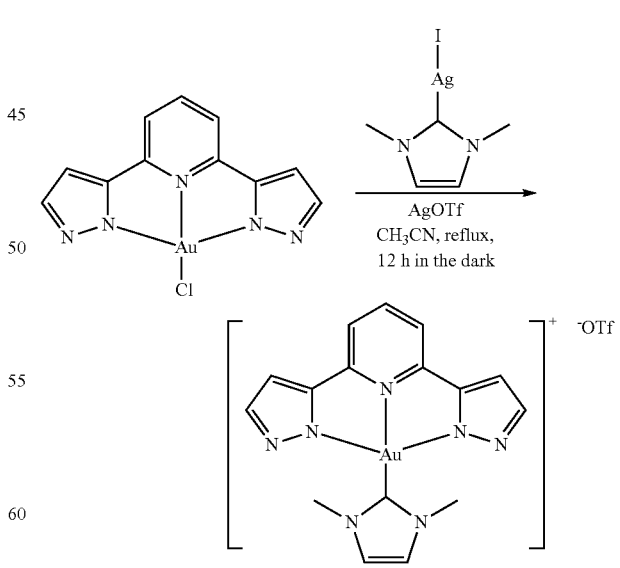

The procedure is similar to that for 1. Yield 40%; ¹H NMR (400 MHz, CD₃CN, 25° C.): δ=8.27 (t, J=8.0 Hz, 1H), 7.76 (d, J=8.0 Hz, 2H), 7.59 (d, J=2.0 Hz, 2H), 7.52 (s, 2H), 6.93 (d, J=1.8 Hz, 2H), 4.01 (s, 6H).

Synthesis of 13

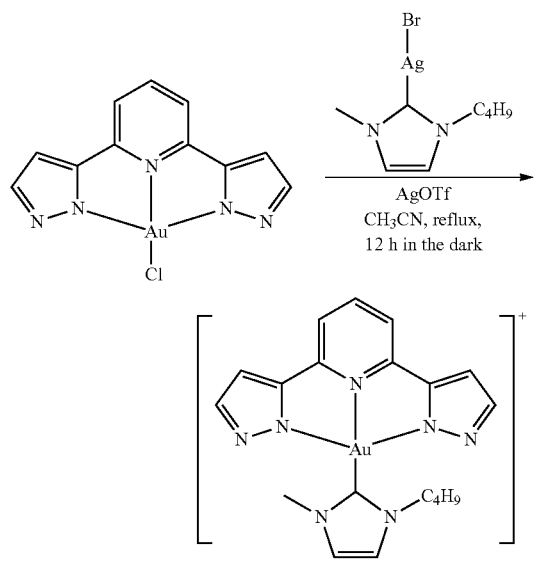

The procedure is similar to that for 1. Yield 42%; $^1$H NMR (300 MHz, CD$_3$CN, 25° C.): δ=8.29 (t, J=8.0 Hz, 1H), 7.79 (d, J=8.0 Hz, 2H), 7.62 (d, J=2.1 Hz, 2H), 7.60 (d, J=2.0 Hz, 1H), 7.57 (d, J=2.0 Hz, 1H), 6.98 (d, J=2.1 Hz, 2H), 4.33 (t, J=7.5 Hz, 2H), 4.01 (s, 3H), 1.86 (m, 2H), 1.28 (m, 2 H), 0.82 (t, J=7.4 Hz, 3H).

Synthesis of 14

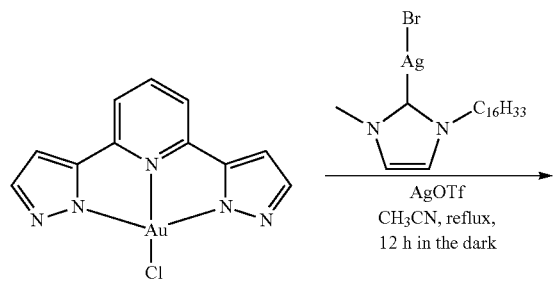

The procedure is similar to that for 1. Yield 38%; $^1$H NMR (400 MHz, CD$_3$CN, 25° C.): δ=8.27 (t, J=8.0 Hz, 1H), 7.76 (d, J=8.0 Hz, 2H), 7.59 (d, J=2.1 Hz, 2H), 7.57 (d, J=2.0 Hz, 1H), 7.54 (d, J=1.9 Hz, 1H), 6.95 (d, J=2.1 Hz, 2H), 4.31 (t, J=7.3 Hz, 2H), 3.99 (s, 3H), 1.86 (m, 2H), 1.30-1.07 (m, 26 H), 0.88 (t, J=6.8 Hz, 3H).

Synthesis of 15

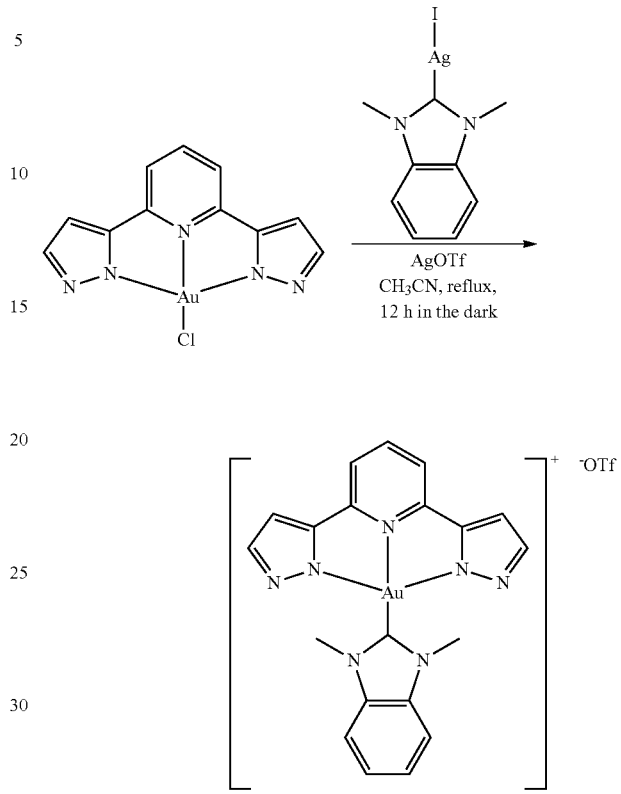

The procedure is similar to that for 1. Yield 40%; $^1$H NMR (300 MHz, CD$_3$CN, 25° C.): δ=8.30 (t, J=8.0 Hz, 1H), 7.87-7.84 (m, 2H), 7.79 (d, J=8.0 Hz, 2H), 7.69-7.65 (m, 2H), 7.59 (d, J=2.1 Hz, 2H), 6.97 (d, J=2.1 Hz, 2H), 4.23 (s, 6H).

Example 6.2

In Vitro Cytotoxicity of the Au(III)-NHC Complexes

Example 2 describes the in vitro cytotoxicity, which is indicative of the induction of cell death and/or inhibition of cellular proliferation of cancer cells, of the Au(III)-NHC complexes on cervical epithelioid carcinoma, hepatocellular carcinoma, leukemia, nasopharyngeal carcinoma, breast carcinoma, melanoma, and lung carcinoma.

By means of MTT assays, the cytotoxic properties of 1-11 were determined toward some established human cancer cell lines including hepatocellular carcinoma (HepG2), cervical epithelioid carcinoma (HeLa), lung carcinoma (NCI-H460), breast cancer (MCF-7), melanoma (B 16) and nasopharyngeal carcinoma (SUNE1). The IC50 values (dose required to inhibit 50% cellular growth for 72 h) of the gold(III) complexes are listed in Table 1. All the Au(III)-NHC complexes exhibit promising cytotoxicity toward these cell lines with $IC_{50}$ values range of 2 to 75 μM. In terms of the $IC_{50}$ values, they display similar cytotoxic properties compared to the reference complexes cisplatin.

TABLE 1

Cytotoxicity $IC_{50}$ of the Au(III)-NHC complexes to selected human cancer cell lines

| Complex | HeLa | HepG2 | NCI-H460 | MCF-7 | SUNE1 | B16 |
|---|---|---|---|---|---|---|
| 1 | 32.9 ± 1.3 | 36.2 ± 2.2 | 55.0 ± 8.5 | 18.4 ± 0.3 | 28.7 ± 7.3 | 30.6 ± 0.3 |
| 2 | 15.7 | 33.2 ± 1.8 | 11.0 ± 0.3 | 17.2 ± 0.6 | 9.9 ± 0.1 | 5.0 ± 0.2 |
| 3 | 14.0 ± 0.3 | 14.7 ± 1.5 | 17.3 ± 0.3 | 8.5 ± 0.2 | 8.9 ± 0.6 | 3.8 ± 0.1 |
| 4 | 8.2 | 11.8 ± 1.2 | 9.7 ± 0.4 | 6.5 ± 0.5 | 5.5 ± 0.3 | 1.6 ± 0.1 |
| 5 | 1.4 ± 0.2 | 3.3 ± 0.5 | 1.4 ± 0.1 | 2.9 ± 0.2 | 28.6 ± 0.3 | 2.2 ± 0.1 |
| 6 | 13.0 ± 1.6 | 28.7 ± 5.9 | 7.9 ± 1.1 | 12.9 ± 2.0 | 9.9 ± 0.2 | 8.3 ± 0.2 |
| 7 | 8.2 | 9.1 ± 0.3 | 34.6 ± 3.1 | 8.6 ± 0.1 | 36.8 ± 1.6 | 7.7 ± 1.0 |
| 8 | 77.4 ± 1.8 | — | 65.4 ± 1.1 | 49.7 ± 3.0 | 47.3 ± 6.2 | 36.8 ± 0.9 |
| 9 | 14.4 | 18.0 ± 0.5 | 11.2 ± 0.7 | 11.9 ± 1.0 | 11.2 ± 0.6 | 12.4 ± 0.1 |
| 10 | 9.2 ± 0.4 | 14.7 ± 1.1 | 5.5 ± 0.3 | 8.7 ± 0.2 | 5.2 ± 1.6 | 5.2 ± 0.2 |
| 11 | 8.4 ± 0.1 | 2.6 ± 0.4 | 5.0 ± 0.1 | 4.0 ± 0.1 | 3.1 ± 0.3 | 5.5 ± 0.1 |
| Cisplatin | 6.4 ± 0.6 | 10.8 ± 0.8 | 1.6 ± 0.3 | 21.8 ± 6.9 | 11.6 ± 2.2 | 12.3 ± 0.7 |

Example 6.3

Induction of Apoptosis by the Au(III)-NHC Complexes Through Inhibition of TrxR Activity Example 3 describes the result of studies showing that complex 9 would induce apoptosis in HeLa cancer cells through inhibition of TrxR activity.

Thioredoxin reductase (TrxR) plays the central role in the thioredoxin system; as a result, large amounts of research have focused on the inhibition of TrxR activity to treat cancer. Although a number of compounds were reported to inhibit purified TrxR, only a few reports showed they can inhibit cell-based TrxR activity.

Electrospray ionization-mass spectrometry (ESI-MS) analysis and $^1$H NMR experiment shows that the Au(III)-NHC complexes can quantitatively react with GSH with 1:3 molar ratio; two equivalent of GSH was oxidized to form GSSG and the remaining one equivalent of GSH was bound to Au(I) (see details in FIG. 3). As Au(I)-NHC complexes are well-known thioredoxin reductase (TrxR) inhibitor, thus they may inhibit the cellular TrxR activity.

Cell-based TrxR activity experiment was incorporated in our experiments. Complex 1, 2, 9 and auronofin were added to HeLa cells and incubated for 1 h, and then the cells were extracted with ice-cold lysis buffer (50 mM phosphate buffer, pH 7.4, 1 mM EDTA, 0.1% Triton-X 100). The cell lysates (10 µg proteins) were added to a buffer (100 µL) containing 100 mM potassium phosphate, pH 7.4, 1 mM EDTA and 0.2 mM NADPH. Reaction was initiated by adding 5,5'-dithiobis (2-nitrobenzoic acid) (DTNB, 3 mM final) and the TrxR activities were determined as increases in O.D. 410 nm in 10 min. It was found that complex 1, 2 and 9 can inhibit cell-based TrxR activity similarly to auranofin (FIG. 4a).

Meanwhile, considerable attention has been paid on apoptosis for which can lead cancer cell death. After treating HeLa cells with 15 µM of complex 9 for 48 h, apoptosis related PARP, caspase 3, 7 and 9 were activated according to western blotting results (FIG. 4b).

Thus the Au(III)-NHC complexes can induce apoptosis of cancer cells, probably caused by the inhibition of TrxR activity (FIG. 4c).

Example 6.4

In Vivo Anti-Cancer Property of the Au(III)-NHC Complexes

Example 4 describes the in vivo tumor inhibition effects of mice bearing HeLa xenograft by complex 5.

Female BALB/cAnN-nu (Nude), 5-7 weeks old, were purchased from the Charles River Laboratories (Wilmington, Mass.) and cared for according to the guidelines of the Laboratory Animal Unit of the University of Hong Kong (HKU). All animal experiments were conducted under the guidelines approved by the Committee on the Use of Live Animals in Teaching and Research of HKU. To establish the HeLa xenograft model, $4 \times 10^6$ HeLa cells suspended in 100 µl of PBS were inoculated into the back flanks of female BALB/cAnN-nu (Nude) mice by subcutaneous injection. When the tumor volumes reached about 50 mm$^3$ (4 days after tumor inoculation), the mice were randomly divided into different treatment groups (3 mg/kg of 5 or solvent control). Complex 5 was reconstituted in PET diluent (60% polyethylene glycol 400, 30% ethanol, 10% Tween 80). Complex 5 dissolved in PET diluent and then diluted in PBS or PBS supplemented with equal amount of PET were injected into the mice by intratumoral injection once every three days until the mice were sacrificed. In this model, the volume of PET diluent injected into each mouse was ≤6 µl. Tumor sizes were measured once every 3 times a week, and tumor volume (V) was calculated by the formula V=ab$^2$×0.52, where a and b were the longest and the shortest diameters of the xenografted tumor. The tumor inhibition was calculated according to the following formula:

$$\text{Inhibition percentage} = [1-(V-V_0)/(V'-V_0')] \times 100\%$$

where V and V' are the tumor volumes of 5 treatment and solvent control, respectively. $V_0$ and $V_0'$ are the initial tumor volumes of the 5 treatment and solvent control, respectively.

Figure 5:
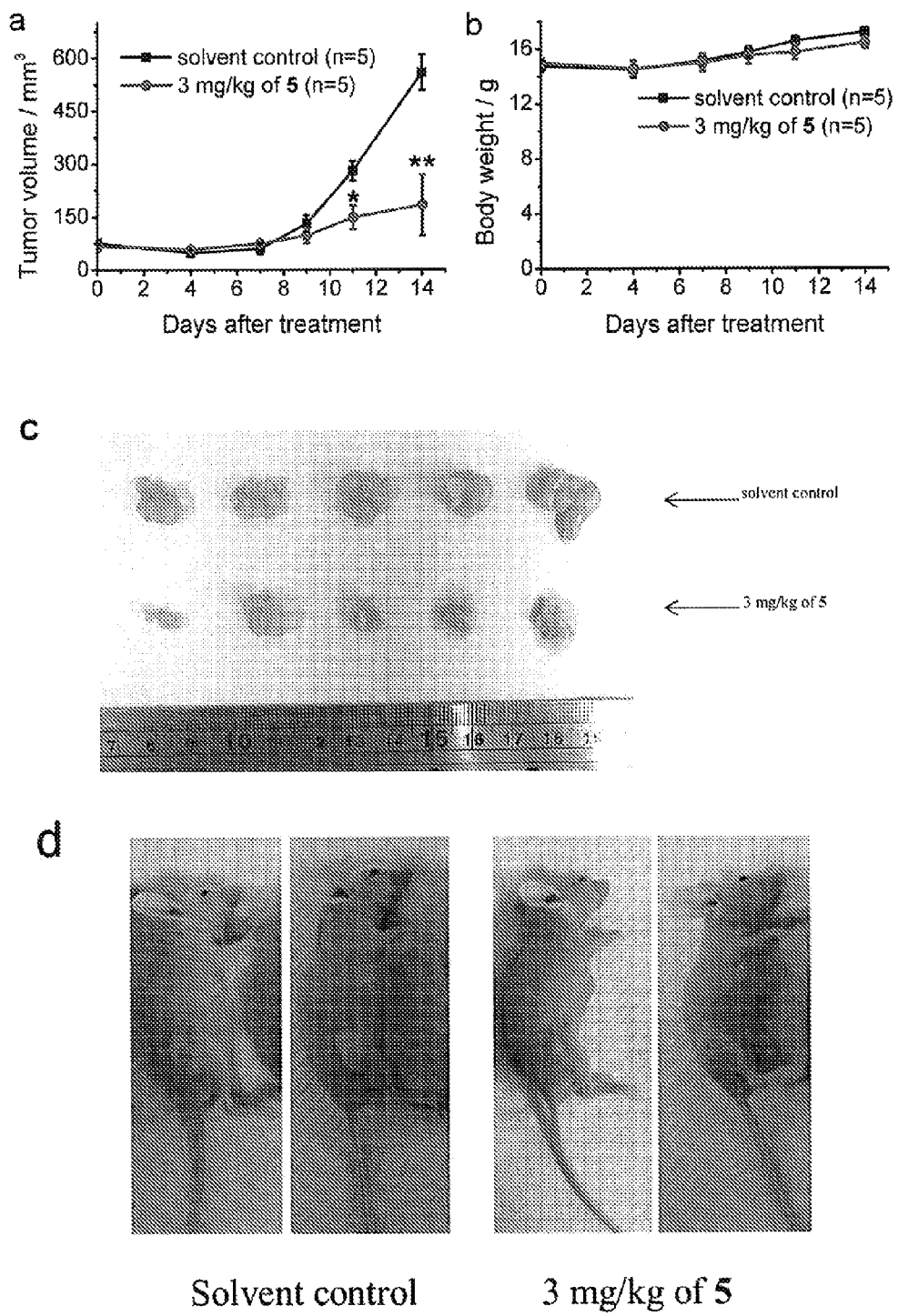

Results shows that after the treatment by 3 mg/kg of 5, significant reduction in tumor volume was found after 11 (p<0.05) and 14 (p<0.01) days, with tumor inhibition up to 60% and 76%, respectively (FIG. 5a, c d). No mouse death or mouse body weight loss was found (FIG. 5b). The slight increase of body weight of mice in the solvent control group might be due to faster growth of the tumors in this group of nude mice.

Preliminary toxicity experiment demonstrated that 20 mg/kg of 5 was toxic to mice while 7 mg/kg caused slight drop of body weight, thus the effective dosage (3 mg/kg) is quite lower than the lethal dosage.

The dosage of the Au(III)-NHC complex is a sufficient amount to inhibit tumor growth and may be dependent on the type of cancer and location of the cancer. This amount may be about 0.1 mg/kg to about 50 mg/kg for mice and humans. Direct intratumoral injection of the Au(III)-NHC complex is preferred. Many pharmaceutical dosage forms are available for administering the Au(III)-NHC complexes. Preferably, pharmaceutical dosage forms suitable for injection or infusion include sterile aqueous solutions or dispersions or sterile powders comprising the Au(III)-NHC complexes which are adapted for facile preparation of sterile injectable or infusible solutions or dispersions are utilized. In all cases, the dosage form should be sterile, fluid and stable under the conditions of manufacture and storage. The liquid carrier or vehicle can be a solvent or liquid dispersion medium comprising, for example, water, ethanol, a polyol, vegetable oil, nontoxic glyceryl esters and suitable mixtures thereof.

What is describe herein is merely illustrative of the Au(III)-NHC complex and their activity. Other embodiments may be implemented by those skilled in the art without departing from the scope and spirit of the present invention.

Example 6.5

Application as Thiol Probe Depending on Fluorescence Changes

Example 5 describes the result of fluorescence changes of 9 towards different analysts and the application for cellular thiol detection and cell imaging.

ESI-MS analysis and $^1$H NMR experiment shows that the Au(III)-NHC complex can quantitatively react with GSH with 1:3 molar ratio, where the N^N^N ligand was released with the formation of GS-Au(I)-NHC compound. As the free N^N^N ligands are highly emissive, thus they may serve as fluorescent switch on probe for thiol detection. Compound 9 was used as an example to detect fluorescence changes towards different analysts and the application as cellular imaging agents.

Fluorescent response towards different Analysts by 9: NaCl, KCl, MgCl$_2$, CaCl$_2$, the amino acids (Ser, Pro, Leu, Ile, His, Ala, Cys), DTT and GSH stock solutions were freshly prepared in 1×PBS:DMSO=9:1 (2 mM). 9 was dissolved in DMSO at room temperature to afford the probe stock solution (10 mM). Then 10 μL of 9 was added to 5 mL of different analyte solutions. The resulting solution was shaken well. After 2 min, the emission spectra were recorded. After 2 h and 12 h, emission intensity has no significant change. For all the measurement, the excitation wavelength was 340 nm and the excitation and emission slit widths were 3 nm. The emission intensity obtained after reacting 9 with each analyte in the aforementioned conditions was measured and compared.

Fluorescence microscopic examination 9: HeLa cells (1×10$^5$ cells) were seeded in a one chamber slide (Nalgene; Nunc) with culture medium (2 mLwell$^{-1}$) and incubated at 37° C. in a humidified atmosphere of 5% CO$_2$/95% air for 24 h. After treating with 9 (20 μM, 1 mL) for 10 min, cells were directly exposed for fluorescent imaging without removing the old medium. The bright-field and fluorescent images (ex: 340 nm) were examined in Axiovert 200 (Carl Zeiss) and in an Axio Vision Rel. 4.5 imaging system (Carl Zeiss).

Figure 6:
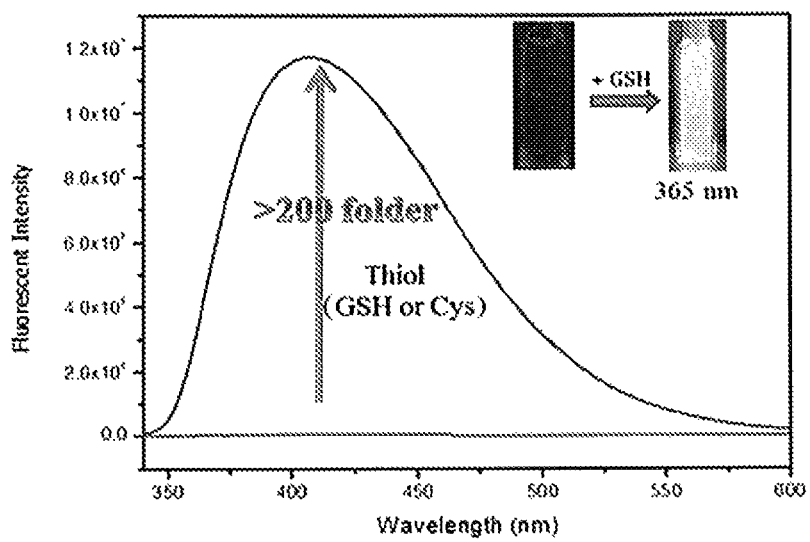
Figure 6:
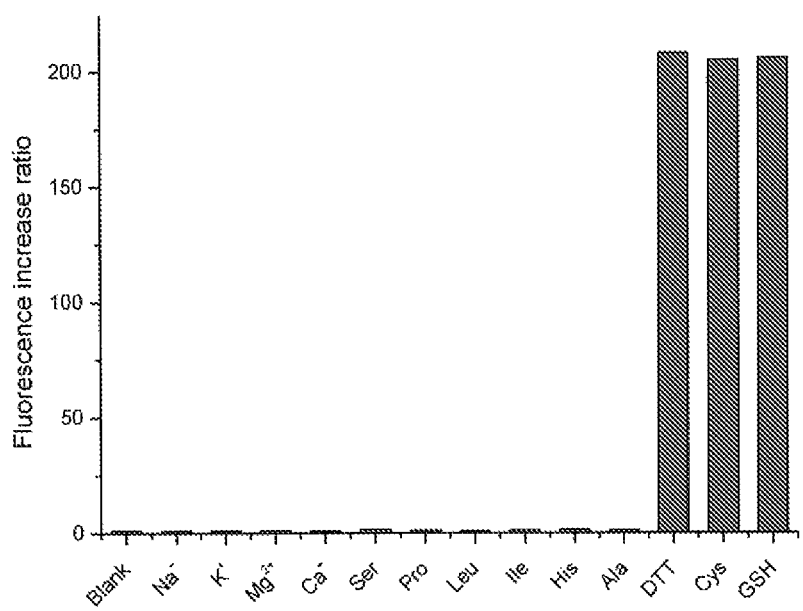
Figure 6:
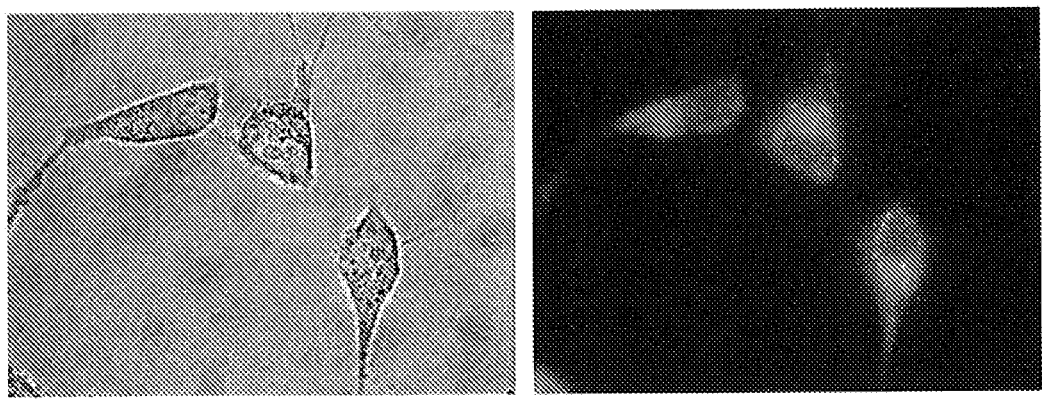

It was found that release of the H$_2$BPB ligand upon treatment of 9 with GSH or Cys led to at least 200-fold increase in emission intensity (FIG. 6). No fluorescence was found when 9 was treated with Na$^+$, K$^+$, Ca$^{2+}$, Mg$^{2+}$, or thiol-free amino acids such as Ala, Ser, Pro, Leu, Ile and His. Complex 9 is sensitive to thiol-containing compounds including GSH, Cys and the commonly used disulfide bond reducing agent dithio-threitol (DTT).

For fluorescence microscopy analysis, it was found that after only 10 min, significant blue fluorescence was detected in cytoplasm but not in nucleus or extracellular environment (FIG. 6), suggestive of the stability of 9 towards cell culture media and efficient activation of Au(III)-NHC complex to Au(I)-NHC in cytoplasm and deliver the active Au(I)-NHC to its molecular target, TrxR.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

References:
[Berners-Price, S. J. et al. *J. Am. Chem. Soc.* 2008, 130, 12570-12571.]

What is claimed is:
1. A composition comprising a compound having the formula I, wherein

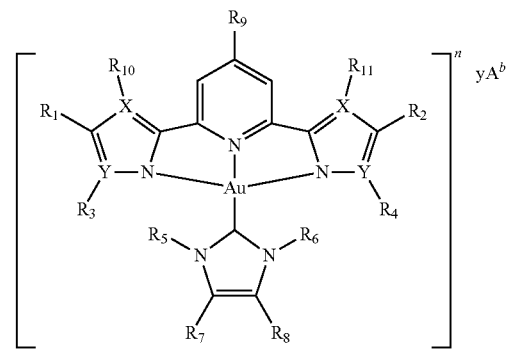

$R_1$, $R_2$, $R_7$, $R_8$, are each independently —H, and $R_3$, $R_4$, $R_{10}$, $R_{11}$ are each independently selected from an electron pair or —H; or each pair of $R_1$ and $R_3$, $R_2$ and $R_4$, $R_7$ and $R_8$, $R_1$ and $R_{10}$, $R_2$ and $R_{11}$ is independently joined together to form

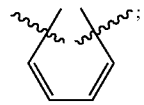 [SMILES: */C=C\C=C/*]

$R_5$, $R_6$, $R_9$, are each independently selected from a —H, —CH$_3$, —C$_4$H$_9$, —C$_6$H$_{13}$, —C$_8$H$_{17}$, —C$_{10}$H$_{21}$, —C$_{16}$H$_{33}$, —C$_3$H$_6$PPh$_3^+$;
n is an integer ranging from +1 to +2;
y is equal to the absolute value of n/b; and
X is selected from a carbon or a nitrogen atom;
Y is selected from a carbon or a nitrogen atom; and
yA$^b$ is a counter-ion.

2. The composition of claim 1, wherein,
X is a nitrogen atom;
Y is a carbon atom;
$R_{10}$, $R_{11}$ are each lone electron pairs;
$R_1$, $R_2$, $R_3$, $R_4$, $R_7$, $R_8$, $R_9$ are each —H;
$R_5$, $R_6$ are each —CH$_3$;
n is +1, and
yA$^b$ is CF$_3$SO$_3^-$.

3. The composition of claim 1, wherein,
X is a nitrogen atom;
Y is a carbon atom;
$R_{10}$, $R_{11}$ are each lone electron pairs;

$R_1$, $R_2$, $R_3$, $R_4$, $R_7$, $R_8$, $R_9$ are each —H;
$R_5$ is —$CH_3$;
$R_6$ is —$C_{49}$;
n is +1, and
$yA^b$ is $CF_3SO_3^-$.

4. The composition of claim 1, wherein,
X is a nitrogen atom;
Y is a carbon atom;
$R_{10}$, $R_{11}$ are each lone electron pairs;
$R_1$, $R_2$, $R_3$, $R_4$, $R_7$, $R_8$, $R_9$ are each —H;
$R_5$ is —$CH_3$;
$R_6$ is —$C_8H_{17}$;
n is +1, and
$yA^b$ is $CF_3SO_3^-$.

5. The composition of claim 1, wherein,
X is a nitrogen atom;
Y is a carbon atom;
$R_{10}$, $R_{11}$ are each lone electron pairs;
$R_1$, $R_2$, $R_3$, $R_4$, $R_7$, $R_8$, $R_9$ are each —H;
$R_5$ is —$CH_3$;
$R_6$ is —$C_{10}H_{21}$,
n is +1, and
$yA^b$ is $CF_3SO_3^-$.

6. The composition of claim 1, wherein,
X is a nitrogen atom;
Y is a carbon atom;
$R_{10}$, $R_{11}$ are each lone electron pairs;
$R_1$, $R_2$, $R_3$, $R_4$, $R_7$, $R_8$, $R_9$ are each —H;
$R_5$ is —$CH_3$;
$R_6$ is —$C_{16}H_{33}$;
n is +1, and
$yA^b$ is $CF_3SO_3^-$.

7. The composition of claim 1, wherein,
X is a nitrogen atom;
Y is a carbon atom;
$R_{10}$, $R_{11}$ are each lone electron pairs;
$R_1$, $R_2$, $R_3$, $R_4$, $R_7$, $R_8$, $R_9$ are each —H;
$R_5$, $R_6$ are each —$C_4H_9$;
n is +1, and
$yA^b$ is $CF_3SO_3^-$.

8. The composition of claim 1, wherein,
X is a nitrogen atom;
Y is a carbon atom;
$R_{10}$, $R_{11}$ are each lone electron pairs;
$R_1$, $R_2$, $R_3$, $R_4$, $R_7$, $R_8$, $R_9$ are each —H;
$R_5$, $R_6$ are each —$C_6H_{13}$;
n is +1, and
$yA^b$ is $CF_3SO_3^-$.

9. The composition of claim 1, wherein,
X is a nitrogen atom;
Y is a carbon atom;
$R_{10}$, $R_{11}$ are each lone electron pairs;
$R_1$, $R_2$, $R_3$, $R_4$, $R_7$, $R_8$, $R_9$ are each —H;
$R_5$ is —$CH_3$;
$R_6$ is —$C_3H_6PPh_3^+$;
n is +2, and
$yA^b$ is $2CF_3SO_3^-$.

10. The composition of claim 1, wherein,
X is a nitrogen atom;
Y is a carbon atom;
Each pair of $R_1$ and $R_3$, and $R_2$ and $R_4$ is joined together to form

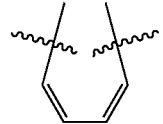 [SMILES: */C=C\C=C/*]

$R_7$, $R_8$, $R_9$ are each —H;
$R_{10}$, $R_{11}$ are each lone electron pairs;,
$R_5$, $R_6$ are each —$CH_3$;
n is +1, and
$yA^b$ is $CF_3SO_3^-$.

11. The composition of claim 1, wherein,
X is a nitrogen atom;
Y is a carbon atom;
Each pair of $R_1$ and $R_3$, and $R_2$ and $R_4$ is joined together to form

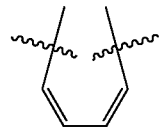 [SMILES: */C=C\C=C/*]

$R_7$, $R_8$, $R_9$ are each —H;
$R_{10}$, $R_{11}$ are each lone electron pairs;
$R_5$, $R_6$ are each —$C_4H_9$;
n is +1, and
$yA^b$ is $CF_3SO_3^-$.

12. The composition of claim 1, wherein,
X is a nitrogen atom;
Y is a carbon atom;
Each pair of $R_1$ and $R_3$, and $R_2$ and $R_4$ is joined together to form

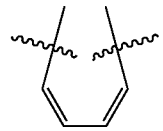 [SMILES: */C=C\C=C/*]

$R_7$, $R_8$, $R_9$ are each —H;
$R_{10}$, $R_{11}$ are each lone electron pairs;
$R_5$, $R_6$ are each —$C_6H_{13}$;
n is +1, and
$yA^b$ is $CF_3SO_3^-$.

13. The composition of claim 1, wherein,
X is a carbon atom;
Y is a nitrogen atom;
$R_3$, $R_4$ are each lone electron pairs;
$R_1$, $R_2$, $R_7$, $R_8$, $R_9$, $R_{10}$, $R_{11}$ are each —H;
$R_5$, $R_6$ are each —$CH_3$;
n is +1, and
$yA^b$ is $OSO_2CF_3^-$.

14. The composition of claim 1, wherein,
X is a carbon atom;
Y is a nitrogen atom;
$R_3$, $R_4$ are each lone electron pairs;
$R_1$, $R_2$, $R_7$, $R_8$, $R_9$, $R_{10}$, $R_{11}$ are each —H;
$R_5$ is —$CH_3$;
$R_6$ is —$C_4H_9$;
n is +1, and
$yA^b$ is $CF_3SO_3^-$.

15. The composition of claim 1, wherein,
X is a carbon atom;
Y is a nitrogen atom;
$R_3$, $R_4$ are each lone electron pairs;
$R_1$, $R_2$, $R_7$, $R_8$, $R_9$, $R_{10}$, $R_{11}$ are each —H;
$R_5$ is —$CH_3$;
$R_6$ is —$C_{16}H_{33}$;
n is +1, and
$yA^b$ is $CF_3SO_3^-$.

16. The composition of claim 1, wherein,
X is a carbon atom;
Y is a nitrogen atom;
$R_3$, $R_4$ are each lone electron pairs;
$R_1$, $R_2$, $R_9$, $R_{10}$, $R_{11}$ are each —H;
$R_7$ and $R_8$ are joined together to form

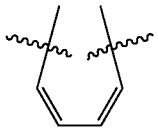

$R_5$, $R_6$ are each —$CH_3$;
n is +1, and
$yA^b$ is $CF_3SO_3^-$.

17. A method of synthesis of the compound of claim 1, comprising: i) reacting $H_2N^{\wedge}N^{\wedge}N$ ligand with $KAuCl_4$ to form $N^{\wedge}N^{\wedge}N$—Au—Cl; and ii) reacting $N^{\wedge}N^{\wedge}N$—Au—Cl with silver triflate (AgOTf) and silver carbene (X—Ag—NHC, X=Cl, Br, or I) to form the compound.

18. The method of claim 17, wherein $H_2N^{\wedge}N^{\wedge}N$ comprise one or more of 2,6-bis(1H-benzo [d] imidazol-2-yl)pyridine ($H_2$BPB), 2,6-di(1H-imidazol-2-yl)pyridine ($H_2$IPI), or 2,6-di(1H-pyrazol-5-yl)pyridine ($H_2$PPP).

19. The method claim 17, wherein $N^{\wedge}N^{\wedge}N$ comprise one or more of deprotonated 2,6-bis(1H-benzo[d]imidazol-2-yl)pyridine (BPB), 2,6-di(1H-imidazol-2-yl)pyridine (IPI), or 2,6-di(1H-pyrazol-5-yl)pyridine)(PPP).

20. A The method of claim 17, wherein the compound comprises a gold(III) atom coordinated to a di-anionic substituted 2,6-bis(1H-benzo[d]imidazol-2-yl)pyridine, 2,6-di(1H-imidazol-2-yl)pyridine, or 2,6-di(1H-pyrazol-5-yl)pyridine ligand and a N-heterocyclic carbene ligand.

21. A method of treating cancer or tumor in a subject comprising administering to said subject an effective amount of the composition of claim 1.

22. The method of claim 21, wherein the cancer treatment is indicated by cell death, inhibition of cellular proliferation, inhibition/poisoning of thioredoxin reductase, inhibition of tumor growth, or a combination thereof.

23. A method of detecting a thiol-containing compound in a sample comprising contacting the sample with the compound in claim 1.

24. The method of claim 21 wherein the preferred amount of the administration of the compound is about 0.1 mg/kg to 50 mg/kg for cancer treatment.

25. The method of claim 21, wherein the cancer is one or more of hepatocellular carcinoma, cervical epithelioid carcinoma, lung carcinoma, breast cancer, melanoma and or nasopharyngeal carcinoma.

26. The method of claim 21, wherein the method is in combination with a second cancer treatment.

27. The method of claim 23, wherein the preferred amount of the compound for thiol detection is 1 µM-500 µM.

28. The method of claim 26, wherein the second cancer treatment is chemotherapy, radiation therapy, gene therapy, surgery or a combination thereof.

29. The method of claim 23 wherein the thiol-containing compound is cysteine, glutathione, or dithiothreitol.

30. A compound having the formula I,

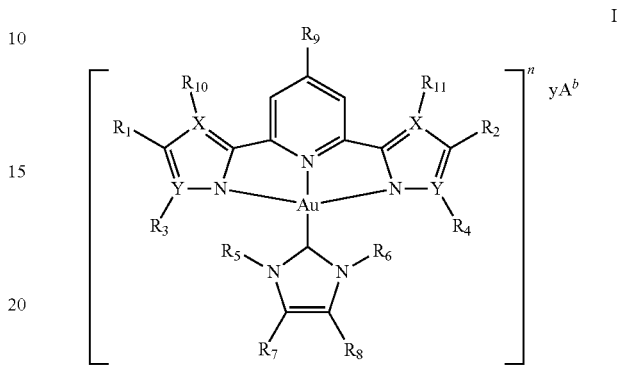

wherein $R_1$, $R_2$, $R_7$, $R_8$, are each independently —H, and $R_3$, $R_4$, $R_{10}$, $R_{11}$ are each independently selected from an electron pair or —H; or each pair of $R_1$ and $R_3$, $R_2$ and $R_4$, $R_7$ and $R_8$, $R_1$ and $R_{10}$, $R_2$ and $R_{11}$ is independently joined together to form

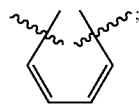

$R_5$, $R_6$, $R_9$, are each independently selected from a —H, —$CH_3$, —$C_4H_9$, —$C_6H_{13}$, —$C_8H_{17}$, —$C_{10}H_{21}$, —$C_{16}H_{33}$, —$C_3H_6PPh_3^+$;
n is an integer ranging from +1 to +2;
y is equal to the absolute value of n/b; and
X is selected from a carbon or a nitrogen atom
Y is selected from a carbon or a nitrogen atom; and yAb is a counter-ion.

31. The method of claim 23, wherein the compound further comprises a fluorescent ligand.

32. The method of claim 23, wherein an increase in the level of a thiol-containing compound in a subject as compared to a control indicates a disease state of the subject.

33. The method of claim 32, wherein the disease is cancer.

34. The composition of claim 1 wherein the counter-ion is fluoride (F—), chloride (Cl—), bromide (Br—), iodide (I—), sulfate (SO42-), phosphate (PO43-), trifluoromethanesulfonate (triflate, —OTf or CF3SO3-), acetate (—OAc), nitrate (NO3-), perchlorate (ClO4-), hexafluorophosphate (PF6-) or hexafluoroacetylacetonate ([CF3C(O)CHC(O)CF3]-).

35. The composition of claim 23, wherein the counter-ion is fluoride (F—), chloride (Cl—), bromide (Br—), iodide (I—), sulfate (SO42-), phosphate (PO43-), trifluoromethanesulfonate (triflate, —OTf or CF3SO3-), acetate (—OAc), nitrate (NO3-), perchlorate (ClO4-), hexafluorophosphate (PF6-) or hexafluoroacetylacetonate ([CF3C(O)CHC(O)CF3]-).

* * * * *

UNITED STATES PATENT AND TRADEMARK OFFICE
CERTIFICATE OF CORRECTION

PATENT NO. : 8,828,984 B2
APPLICATION NO. : 14/078742
DATED : September 9, 2014
INVENTOR(S) : Chi Ming Che and Taotao Zou It is certified that error appears in the above-identified patent and that said Letters Patent is hereby corrected as shown below:

Title page, item (71) Applicant: "University of Hong Kong, Hong Kong (CN)" should be
--The University of Hong Kong, Hong Kong (CN)--

Signed and Sealed this
Twenty-third Day of February, 2016

Michelle K. Lee
*Director of the United States Patent and Trademark Office*